(12) United States Patent
Bresina et al.

(10) Patent No.: US 7,585,287 B2
(45) Date of Patent: Sep. 8, 2009

(54) DEVICE AND METHOD FOR INSERTION OF A CANNULA OF AN INFUSION DEVICE

(75) Inventors: Timothy Bresina, Shoreview, MN (US);
Steve Albert Cote, Stillwater, MN (US);
Mark Faust, Lino Lakes, MN (US);
James Marrs, Arden Hills, MN (US);
Keith Williams, Sumerset, WI (US)

(73) Assignee: Smiths Medical MD, Inc., St. Paul, MN (US)

( * ) Notice: Subject to any disclaimer, the term of this patent is extended or adjusted under 35 U.S.C. 154(b) by 331 days.

(21) Appl. No.: 10/869,181

(22) Filed: Jun. 16, 2004

(65) Prior Publication Data

US 2005/0283114 A1 Dec. 22, 2005

(51) Int. Cl.
*A61M 31/00* (2006.01)

(52) U.S. Cl. ............... 604/93.01; 604/506; 604/164.01; 604/181; 604/198; 604/164.12

(58) Field of Classification Search ................. 604/513, 604/506, 157, 180, 117, 158, 160, 171, 135, 604/137, 198, 164.01, 181, 110, 93.01, 164.04, 604/134, 136, 263, 264, 164.12, 181.11, 604/134.136
See application file for complete search history.

(56) References Cited

U.S. PATENT DOCUMENTS

| | | | |
|---|---|---|---|
| 3,094,989 A * | 6/1963 | Ferdinand | 604/138 |
| 3,547,119 A | 12/1970 | Hall et al. | |
| 4,531,937 A | 7/1985 | Yates | |
| 4,755,173 A | 7/1988 | Konopka et al. | |
| 4,994,042 A | 2/1991 | Vadher | |
| 5,092,853 A | 3/1992 | Couvertier, II | |
| 5,129,884 A | 7/1992 | Dysarz | |
| 5,135,496 A | 8/1992 | Vetter | |
| 5,137,516 A * | 8/1992 | Rand et al. | 604/136 |
| 5,167,632 A * | 12/1992 | Eid et al. | 604/136 |

(Continued)

FOREIGN PATENT DOCUMENTS

DE 299 05 072 U1 9/1999

(Continued)

OTHER PUBLICATIONS

"inset® Visual Guide," *Unomedical*, 16 pages (© 2004).

*Primary Examiner*—Nicholas D Lucchesi
*Assistant Examiner*—Quynh-Nhu H Vu
(74) *Attorney, Agent, or Firm*—Merchant & Gould P.C.

(57) ABSTRACT

A device for inserting a subcutaneous infusion device into skin of a patient. The device can include a housing, a needle hub including a needle, a sleeve, and a spring engaging the needle hub. The device can also include a cap coupled to the housing, and a retention member configured to maintain the device in a ship state prior to decoupling of the cap from the housing. In one example, the retention member can include a boss coupled to the cap and configured to engage the infusion device to maintain the infusion device in the ship state prior to decoupling of the cap from the housing. In another example, the retention member can include a tab formed by the sleeve, the tab engaging a bead on an internal surface of the cap when the sleeve moves relative to the housing while the device is in the ship state.

12 Claims, 27 Drawing Sheets

U.S. PATENT DOCUMENTS

| | | | |
|---|---|---|---|
| 5,176,650 A | 1/1993 | Haining | |
| 5,176,662 A * | 1/1993 | Bartholomew et al. | 604/513 |
| 5,257,980 A | 11/1993 | Van Antwerp et al. | |
| 5,522,803 A | 6/1996 | Teissen-Simony | |
| 5,545,143 A | 8/1996 | Fischell | |
| 5,573,510 A | 11/1996 | Isaacson | |
| 5,575,777 A | 11/1996 | Cover et al. | |
| 5,584,813 A | 12/1996 | Livingston et al. | |
| 5,591,188 A | 1/1997 | Waisman | |
| 5,676,156 A | 10/1997 | Yoon | |
| 5,738,641 A | 4/1998 | Watson | |
| 5,833,666 A | 11/1998 | Davis | |
| 5,848,990 A | 12/1998 | Cirelli et al. | |
| 5,851,197 A | 12/1998 | Marano et al. | |
| 5,873,856 A * | 2/1999 | Hjertman et al. | 604/117 |
| 5,968,011 A | 10/1999 | Larsen et al. | |
| 5,980,506 A | 11/1999 | Mathiasen | |
| 6,017,328 A | 1/2000 | Fischell et al. | |
| 6,056,718 A | 5/2000 | Funderburk et al. | |
| 6,056,726 A | 5/2000 | Isaacson | |
| 6,077,244 A | 6/2000 | Botich et al. | |
| 6,086,575 A | 7/2000 | Mejslov | |
| 6,093,172 A | 7/2000 | Funderburk et al. | |
| 6,123,690 A | 9/2000 | Mejslov | |
| 6,159,181 A | 12/2000 | Crossman et al. | |
| 6,293,925 B1 | 9/2001 | Safabash et al. | |
| 6,302,866 B1 | 10/2001 | Marggi | |
| 6,355,021 B1 | 3/2002 | Nielsen et al. | |
| 6,450,992 B1 | 9/2002 | Cassidy, Jr. | |
| 6,517,517 B1 * | 2/2003 | Farrugia et al. | 604/131 |
| 6,520,938 B1 | 2/2003 | Funderburk et al. | |
| 6,572,586 B1 | 6/2003 | Wojcik | |
| 6,579,267 B2 | 6/2003 | Lynch et al. | |
| 6,607,509 B2 | 8/2003 | Bobroff et al. | |
| 6,613,064 B2 * | 9/2003 | Rutynowski et al. | 606/185 |
| 6,685,674 B2 | 2/2004 | Douglas et al. | |
| 6,736,797 B1 | 5/2004 | Larsen et al. | |
| 6,926,694 B2 | 8/2005 | Morano-Ford | |
| 7,018,344 B2 | 3/2006 | Bressler et al. | |
| 7,052,483 B2 | 5/2006 | Wojcik | |
| 7,056,302 B2 | 6/2006 | Douglas | |
| 2001/0053889 A1 | 12/2001 | Marggi et al. | |
| 2002/0045867 A1 | 4/2002 | Nielsen et al. | |
| 2002/0077599 A1 | 6/2002 | Wojcik | |
| 2002/0161332 A1 | 10/2002 | Ramey | |
| 2002/0173769 A1 | 11/2002 | Gray et al. | |
| 2003/0014018 A1 * | 1/2003 | Giambattista et al. | 604/198 |
| 2003/0060776 A1 * | 3/2003 | Heiniger | 604/198 |
| 2003/0060781 A1 * | 3/2003 | Mogensen et al. | 604/257 |
| 2003/0109829 A1 | 6/2003 | Mogensen et al. | |
| 2003/0125669 A1 | 7/2003 | Safabash et al. | |
| 2003/0130619 A1 | 7/2003 | Safabash et al. | |
| 2003/0158520 A1 | 8/2003 | Safabash et al. | |
| 2003/0199823 A1 | 10/2003 | Bobroff et al. | |
| 2003/0225373 A1 | 12/2003 | Bobroff et al. | |
| 2003/0225374 A1 | 12/2003 | Mathiasen | |
| 2004/0002682 A1 | 1/2004 | Kovelman et al. | |
| 2004/0143216 A1 | 7/2004 | Douglas et al. | |
| 2004/0158207 A1 * | 8/2004 | Hunn et al. | 604/164.01 |
| 2004/0199123 A1 | 10/2004 | Nielsen | |
| 2004/0204687 A1 | 10/2004 | Mogensen et al. | |
| 2004/0260250 A1 | 12/2004 | Harris et al. | |
| 2005/0043687 A1 | 2/2005 | Mogensen et al. | |
| 2005/0075606 A1 | 4/2005 | Botich et al. | |
| 2005/0101933 A1 | 5/2005 | Marrs | |
| 2005/0107743 A1 | 5/2005 | Fangrow | |
| 2005/0131346 A1 | 6/2005 | Douglas | |
| 2006/0041224 A1 | 2/2006 | Jensen | |
| 2006/0173413 A1 | 8/2006 | Fan | |

FOREIGN PATENT DOCUMENTS

| | | |
|---|---|---|
| DE | 202 20 543 U1 | 10/2003 |
| EP | 0 290 176 A1 | 11/1988 |
| EP | 0 239 244 B1 | 9/1991 |
| EP | 0 451 040 A1 | 10/1991 |
| EP | 0 615 768 B1 | 12/1999 |
| EP | 1 329 233 A1 | 7/2003 |
| WO | WO 02/081012 A2 | 10/2002 |

\* cited by examiner

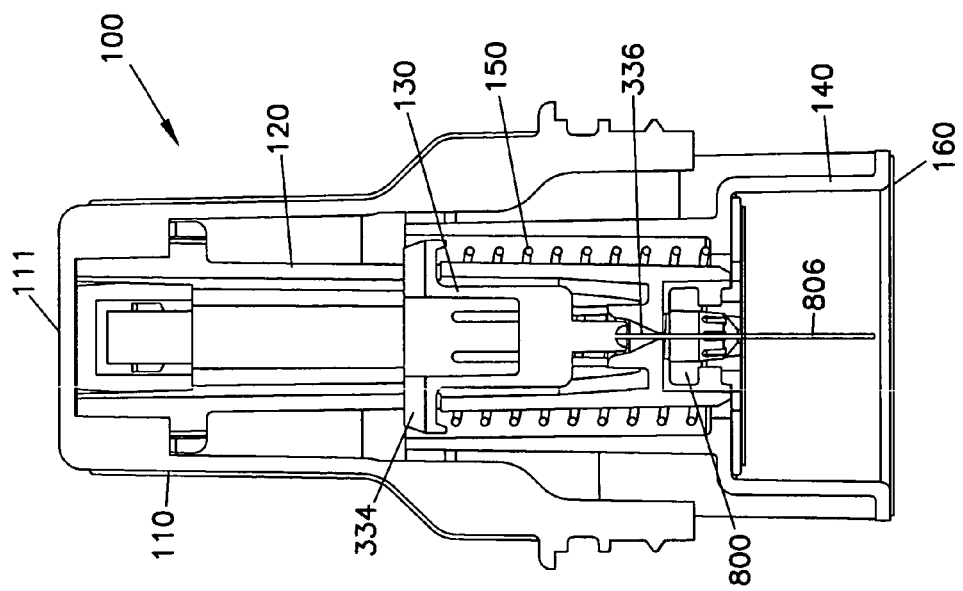
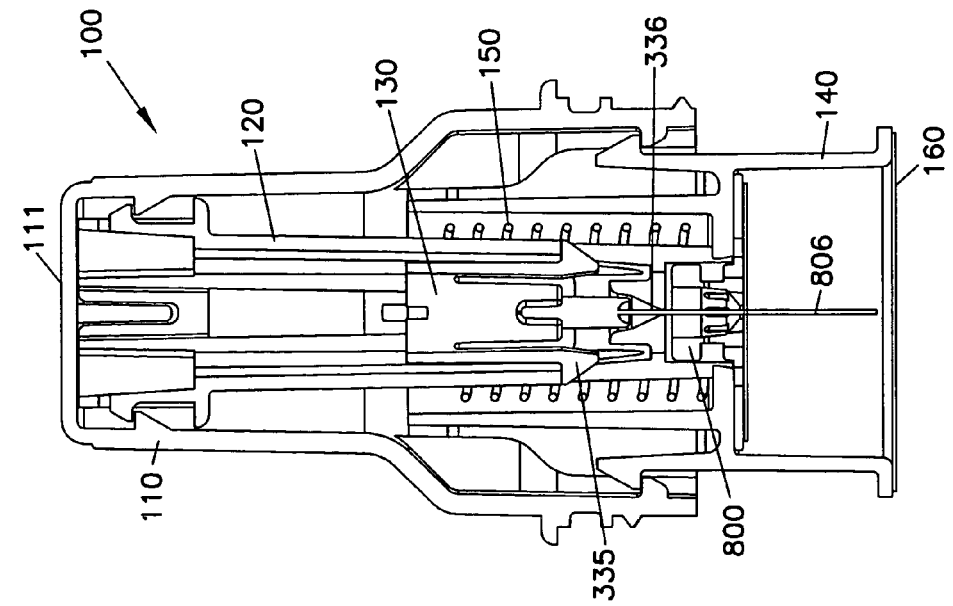

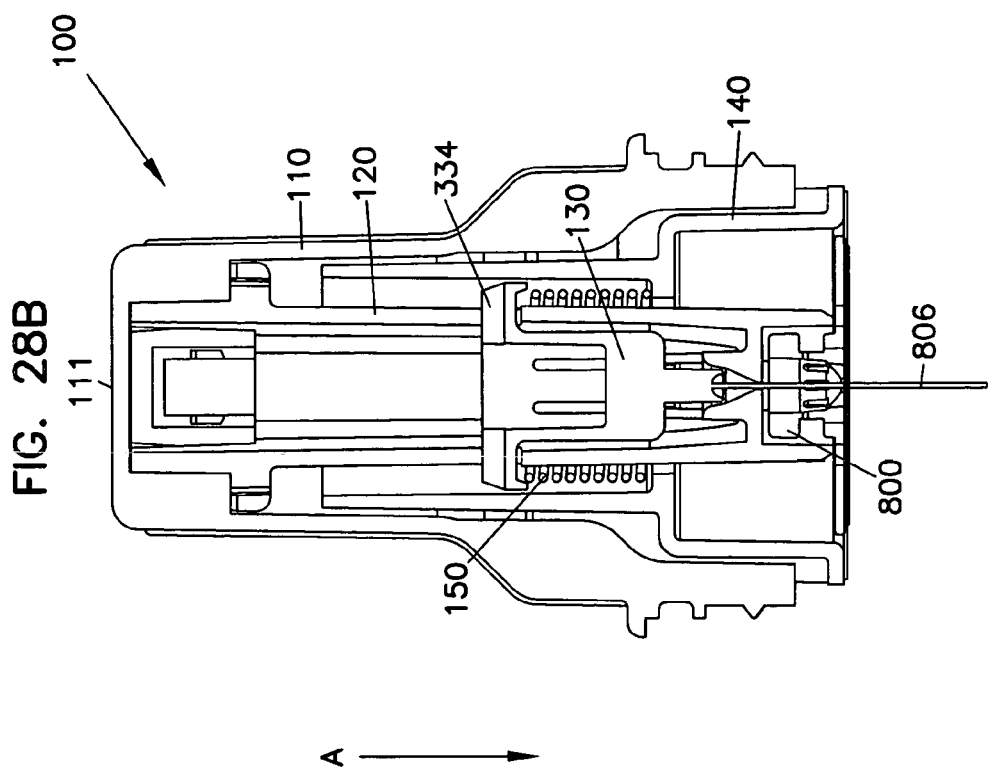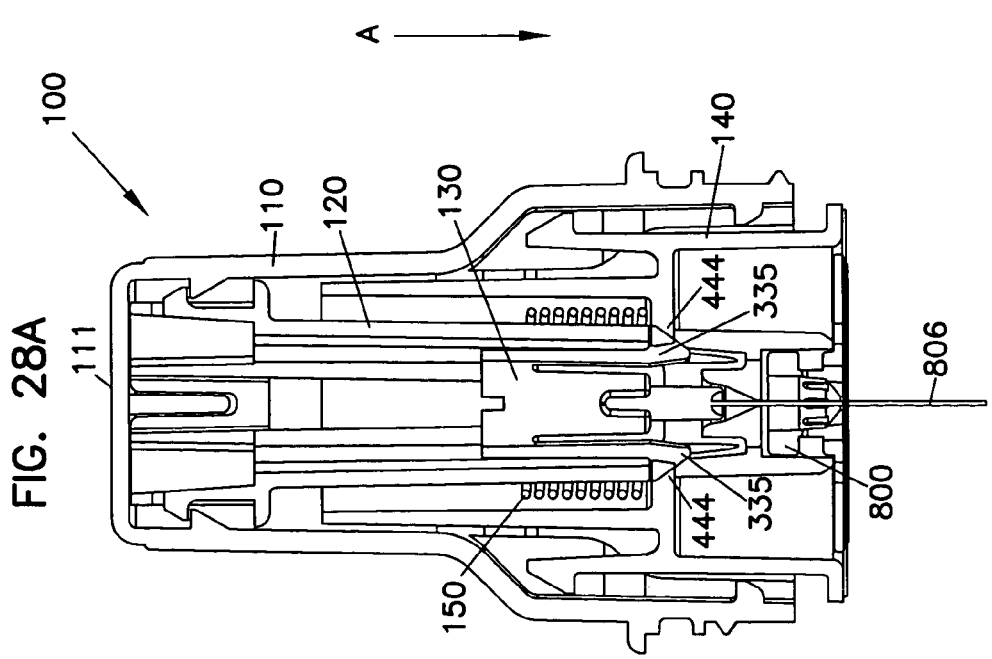

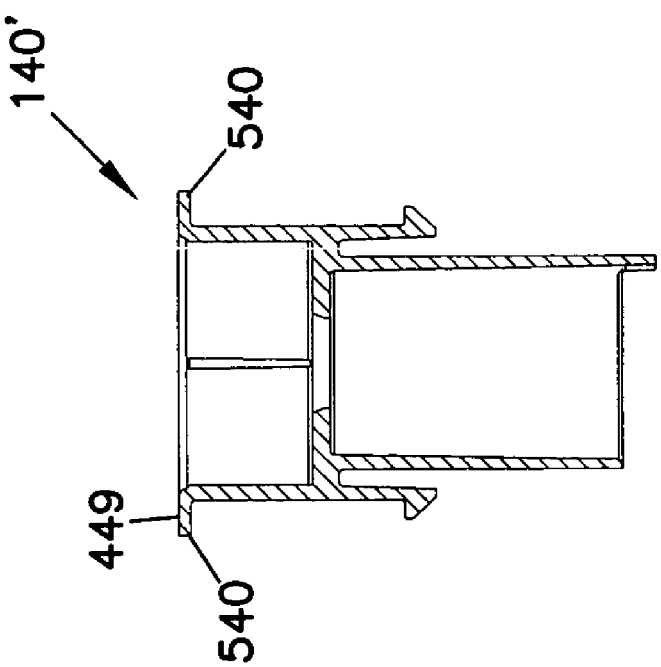
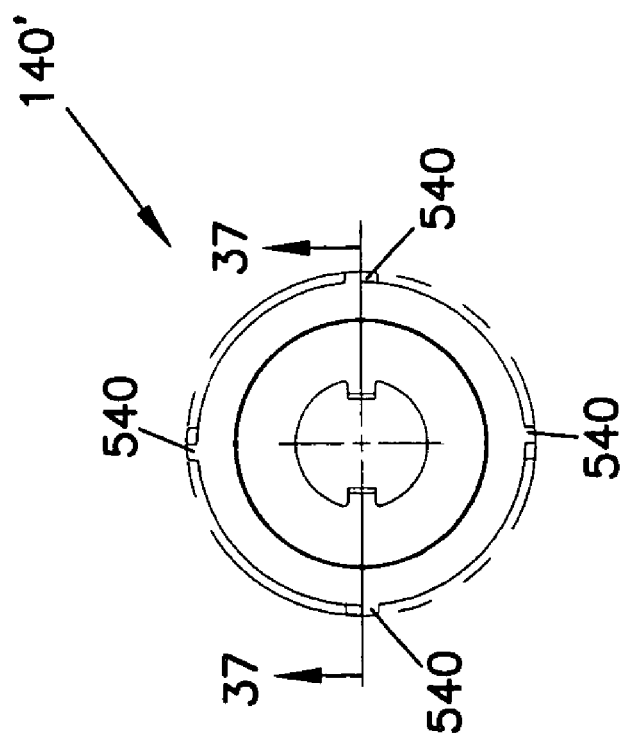

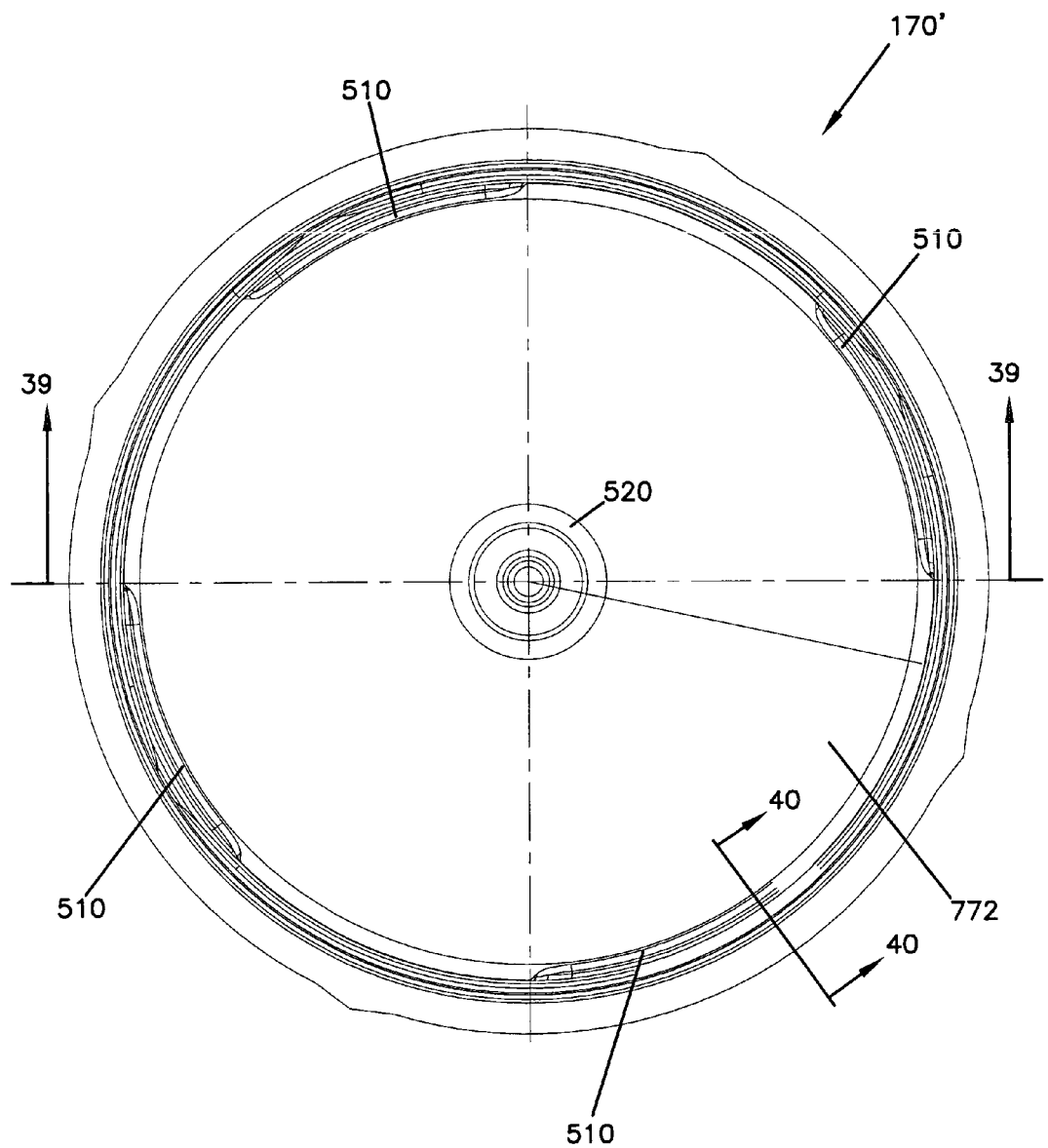

DEVICE AND METHOD FOR INSERTION OF A CANNULA OF AN INFUSION DEVICE

TECHNICAL FIELD

The present invention relates to a device for assisting in the introduction of a cannula of an infusion device into the skin of a patient for delivery of a substance to the patient.

BACKGROUND

Infusion devices are used to deliver substances such as medications into the subcutaneous layer of skin of a patient. Devices for assisting in insertion of the cannula of an infusion device into the skin of the patient are known. For example, some devices utilize springs to automatically drive a needle into the skin of a patient to introduce the cannula of the infusion device into the subcutaneous layer.

Because a needle is used to introduce the cannula of the infusion device into the subcutaneous layer of skin, there is a risk associated with inadvertent exposure to the needle. Further, patients may react adversely to viewing the needle prior to insertion and may, for example, be reluctant to place the needle into the skin. Prior devices may not adequately shroud this needle prior to and/or after introduction of the infusion device.

Other issues of concern in the design and use of insertion devices include ease of use by the patient and sterilization. For example, some patients may have difficulty loading the infusion device into the insertion device.

It is therefore desirable to provide new designs for devices used to assist in the introduction of an infusion device into the skin of a patient.

SUMMARY

Embodiments made in accordance with the present invention include devices that can be used to assist in the introduction of the cannula of an infusion device into the skin of a patient for delivery of a substance to the patient.

For example, one embodiment of a device includes a needle used to insert the cannula of an infusion device into the skin of a patient. Once the cannula of the infusion device is inserted into the skin, the device moves the needle to a retracted state within the device.

In another embodiment, a device is configured to move a needle and associated cannula of an infusion device from a delivery state to a trigger state at which the cannula of the infusion device is inserted into the skin of a patient. Upon full insertion of the cannula at the trigger state, the device is then configured to move the needle to a retracted state within the device.

In another embodiment, a device includes a needle that can be used to insert a cannula of a site into the skin of a patient. Upon insertion of the cannula, the needle can be removed from the skin. In one embodiment, a cap is provided that can be placed onto the device prior to and after use of the device to provide a sterile environment and/or to reduce exposure to the needle.

In another embodiment, a device includes features that retain components of the device and site contained therein in desired positions while the device is in a ship state. In an example embodiment, the device can include tabs on a sleeve that engage beads on a cap to retain the sleeve in a desired position with respect to a housing while in the device is in a ship state. In an example embodiment, the device can also include a boss formed by the cap to retain the site at a desired position with respect to a needle of the device while the device is in the ship state.

The above summary of the present invention is not intended to describe each disclosed embodiment or every implementation of the present invention. Figures in the detailed description that follow more particularly exemplify embodiments of the invention. While certain embodiments will be illustrated and described, the invention is not limited to use in such embodiments.

DESCRIPTION OF THE DRAWINGS

FIG. 27A is a cross-sectional view taken along line 27A-27A of the device of FIG. 24 in a delivery state.

FIG. 27B is a cross-sectional view taken along line 27B-27B of the device of FIG. 24 in the delivery state.

FIG. 28A is a cross-sectional view taken along line 28A-28A of the device of FIG. 25 in a trigger state.

FIG. 28B is a cross-sectional view taken along line 28B-28B of the device of FIG. 25 in the trigger state.

FIG. 36 is an end view of the sleeve of FIG. 34.

FIG. 37 is a cross-sectional view taken along line 37-37 of the sleeve of FIG. 36.

FIG. 38 is an end view of a cap of the device of FIG. 31.

DETAILED DESCRIPTION

Embodiments of the present invention relate to devices for assisting in the introduction of an infusion device, specifically a cannula of the infusion device, into the subcutaneous layer of skin of a patient.

Figure 1:
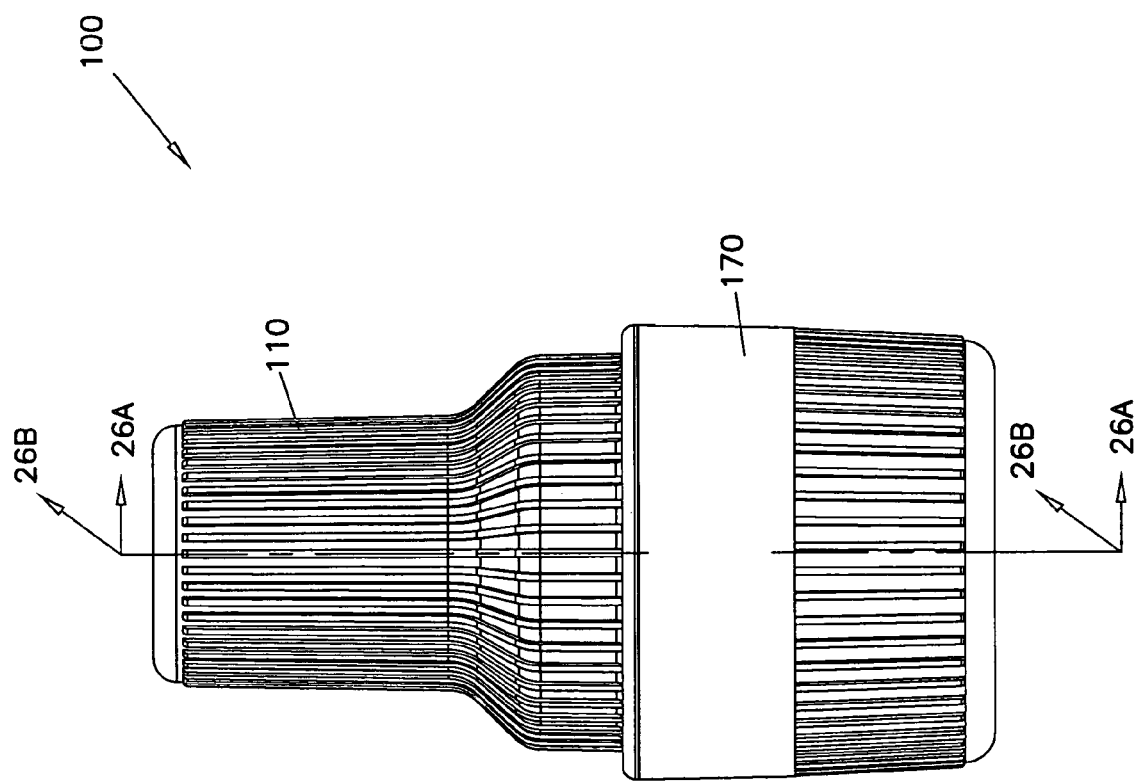
FIG. 1 is a side view of an example embodiment of a device used to introduce a cannula of an infusion device into a patient made in accordance with the present invention.
Figure 2:
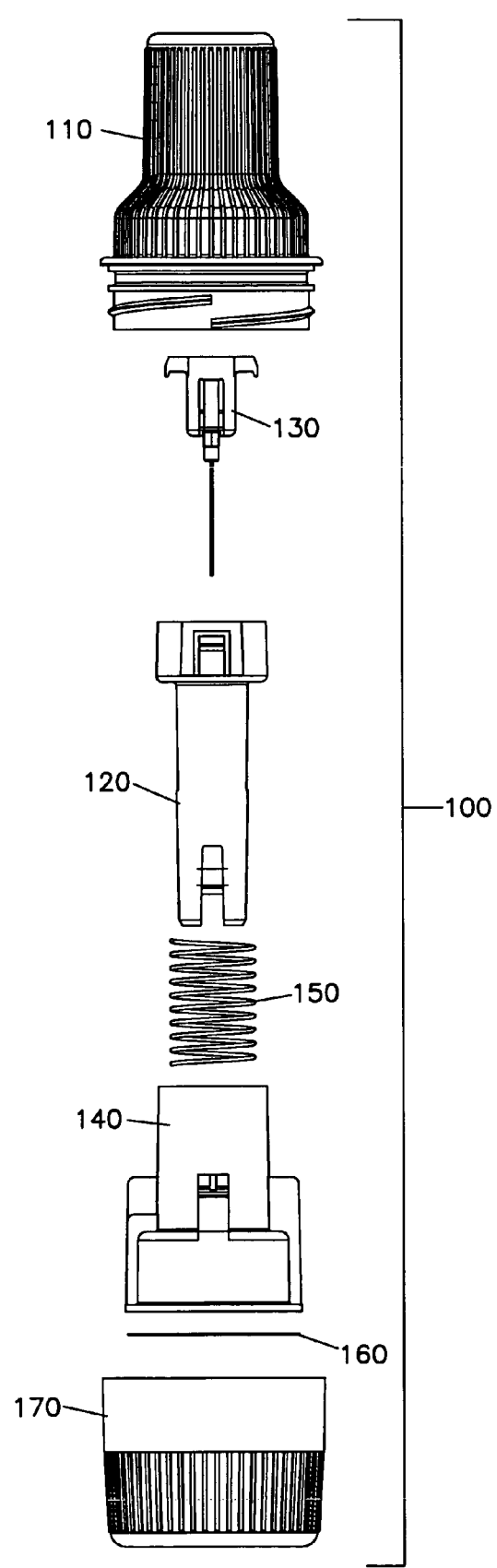
FIG. 2 is an exploded side view of the device of FIG. 1.

Referring to FIGS. 1 and 2, one example embodiment of a device 100 is shown. The device 100 is used to introduce a cannula of an infusion device, such as a set, site, or other access device, into the skin of the patient. The set, site, or other access device can then be used to deliver drugs or other fluid to the patient, such as from an infusion pump.

The device 100 generally includes a housing 110, a cylinder hub 120, a needle hub 130, a sleeve 140, a spring 150, an adhesive portion 160, and a cap 170. Each of the components of the device 100, described further below, is configured to assist in the introduction of a cannula of an infusion device into the skin of a patient.

Figure 3:
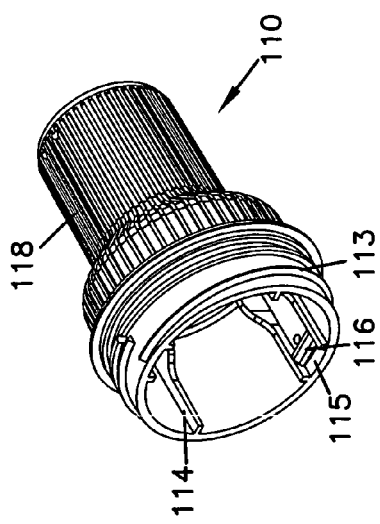
FIG. 3 is a perspective view of a housing of the device of FIG. 1.
Figure 4:
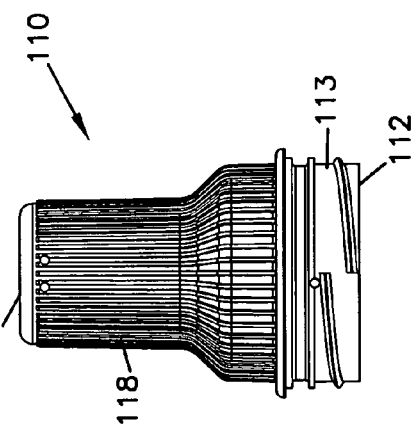
FIG. 4 is a side view of the housing of FIG. 3.
Figure 5:
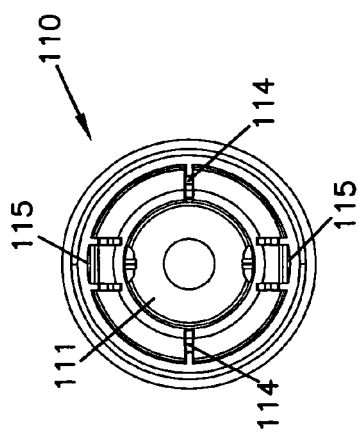
FIG. 5 is an end view of the housing of FIG. 3.
Figure 7:
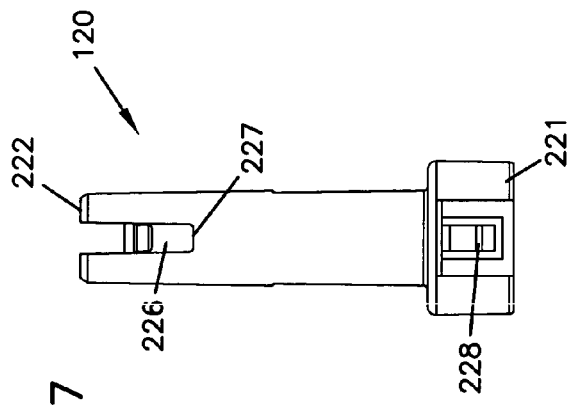
FIG. 7 is side view of the cylinder hub of FIG. 6.
Figure 9:
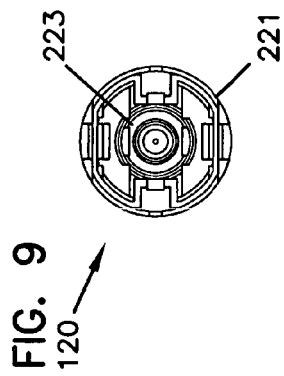
FIG. 9 is an end view of the cylinder hub of FIG. 6.
Figure 6:
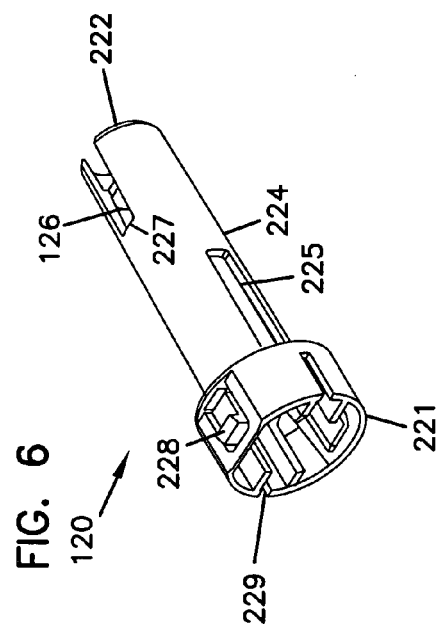
FIG. 6 is a perspective view of a cylinder hub of the device of FIG. 1.
Figure 8:
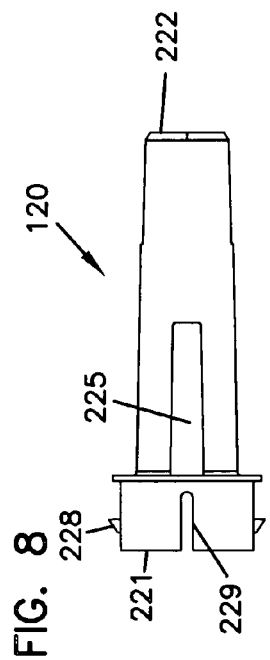
FIG. 8 is another side view of the cylinder hub of FIG. 6.
Figure 13:
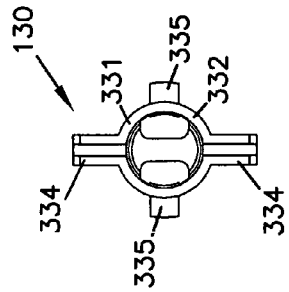
FIG. 13 is an end view of the needle hub of FIG. 10.
Figure 11:
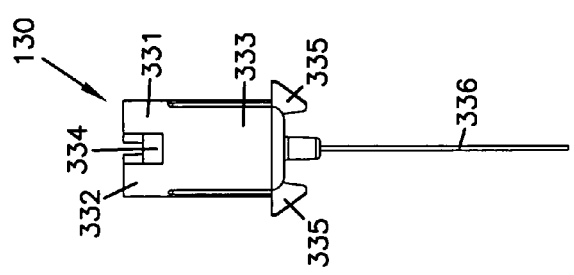
FIG. 11 is a side view of the needle hub of FIG. 10.
Figure 12:
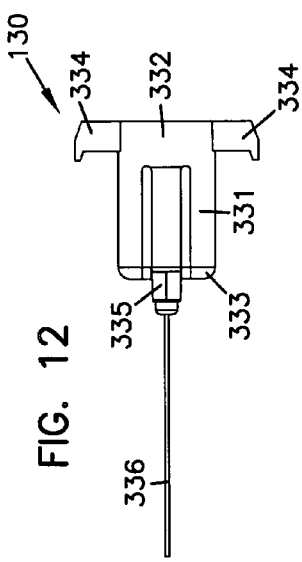
FIG. 12 is another side view of the needle hub of FIG. 10.
Figure 10:
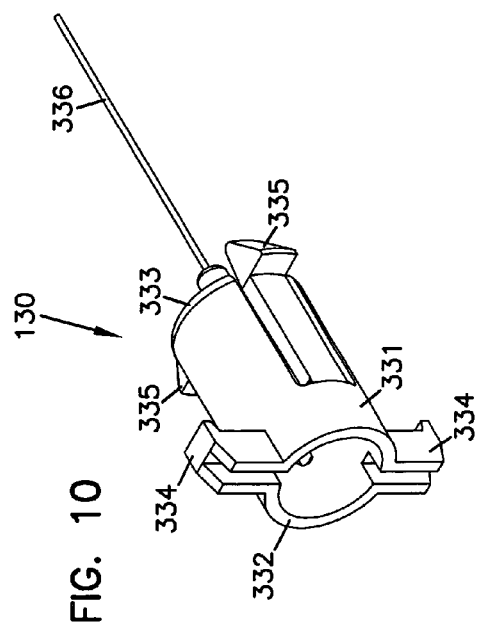
FIG. 10 is a perspective view of a needle hub of the device of FIG. 1.

Referring now to FIGS. 3-5, the housing 110 is shown. The housing 110 is preferably cylindrical in shape and includes a closed upper end 111 and an open lower end 112. The housing 110 further preferably includes a portion 118 with a knurled surface to enhance a patient's grip on the housing 110, as well as a threaded portion 113 positioned adjacent the open lower end 112.

Referring now to FIGS. 6-9, the cylinder hub 120 is shown in greater detail. The cylinder hub 120 includes first and second ends 221 and 222 and an interior passage 223. In addition, two opposing slots 225 are formed on opposite sides of the cylinder hub 120 and generally extend from a mid-portion 224 of the hub 120 to the first end 221. Further, the cylinder hub 120 includes opposing apertures 226 formed in the cylinder hub 120 adjacent the second end 222.

The first end 221 of the cylinder hub 120 is coupled to the upper end 111 of the housing 110 by tabs 119 on the housing 110 engaging shoulders 228 formed by the cylinder hub 120. See, for example, FIGS. 6-8, 26A, and 26B. In addition, members 121 of the housing 110 are received in slots 229 of the cylinder hub 120. In alternative designs, the housing 110 and cylinder hub 120 can be formed as a single unit.

Referring now to FIGS. 10-13, the needle hub 130 includes a main body 331 with first and second ends 332 and 333, and a needle 336 (hollow or solid) coupled to the main body 331. The main body 331 includes opposing wings 334 formed at the first end 332 and opposing barbs 335 at the second end 333.

The needle hub 130 is positioned in the interior passage 223 of the cylinder hub 120 such that the opposing wings 334 of the needle hub 130 extend through the opposing slots 225 of the cylinder hub 120. See FIGS. 6, 8, 26B, 27B, 28B, 29B, and 30B. In addition, the opposing barbs 335 of the needle hub 130 extend through the opposing apertures 226 of the cylinder hub 120 and engage shoulders 227 formed by the apertures 226 so that the needle hub 130 is held in a fixed position relative to the cylinder hub 120 and the housing 110. See, for example, FIGS. 6, 8, 26A, 27A, and 28A.

Referring now to FIGS. 14-17, the sleeve 140 is shown. The sleeve 140 is preferably cylindrical in shape and includes first and second ends 441 and 442 and interior passage 443. Opposing projections 444 extend into the passage 443 adjacent to a shoulder 445. On the exterior of the sleeve 140 channels 446 are formed, as well as railways 447 with barbs 448 formed on ends thereof.

The sleeve 140 is coupled to the housing 110 such that the housing 110 can be moved longitudinally with respect to the sleeve 140. Specifically, the railways 114 of the housing are received in the channels 446 of the sleeve 140. Likewise, the railways 447 of the sleeve 140 are received in the channels 115 of the housing 110. Barbs 448 on the railways 447 of the sleeve 140 engage projections 116 in the channels 115 of the housing 110 so that the housing 110 remains slideably coupled to the sleeve 140 in opposition to the force exerted by the spring 150 (described further below).

The spring 150 includes first and second ends 152 and 154. See, for example, FIG. 26B. The spring 150 surrounds a portion of the cylinder hub 120 and extends within the passage 443 of the sleeve 140. The first end 152 of the spring 150 is seated on the shoulder 445 of the sleeve 140, and the second end 154 of the spring 150 engages the opposing wings 334 of the needle hub 130 extending through the opposing slots 225 of the cylinder hub 120.

The spring 150 is in a compressed state as shown in FIGS. 26A, 26B, 27A, 27B, 28A, and 28B and therefore applies force against the wings 334 of the needle hub 130, biasing the needle hub 130 in an upward direction. However, barbs 335 of the main body 331 of the needle hub 130 are engaged against shoulders 227 of the apertures 226 of the cylinder hub 120 to retain the needle hub 130 in place with respect to the cylinder hub 120. See, for example, FIG. 26A. Likewise, the spring 150 forces the housing 110 and the sleeve 140 apart until barbs 448 of the sleeve 140 engage projections 115 of the housing 110 to maintain coupling between the housing 110 and the sleeve 140.

Figure 17:
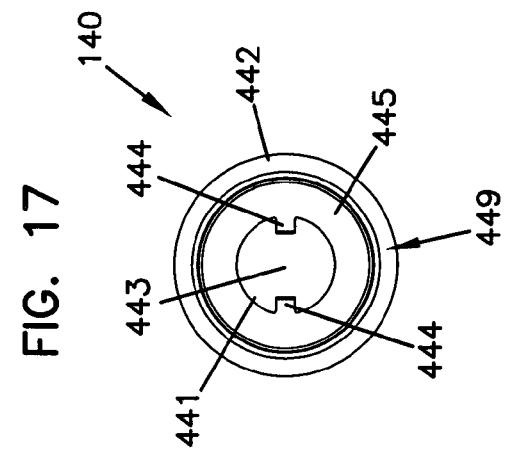
FIG. 17 is an end view of the sleeve of FIG. 14.
Figure 15:
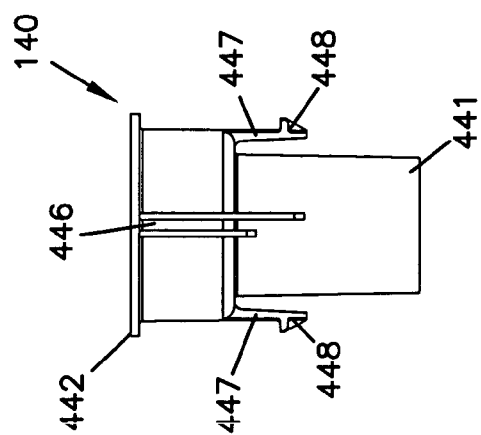
FIG. 15 is a side view of the sleeve of FIG. 14.
Figure 16:
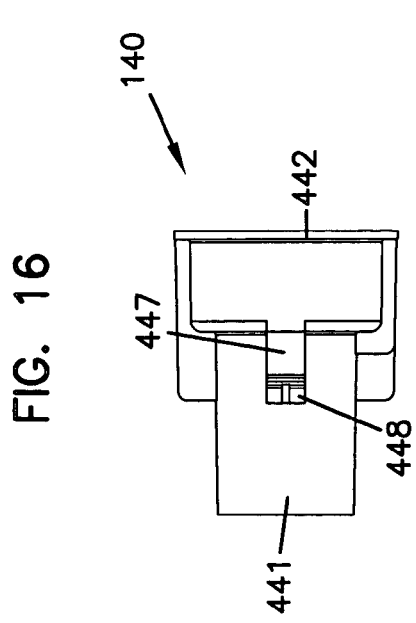
FIG. 16 is another side view of the sleeve of FIG. 14.
Figure 14:
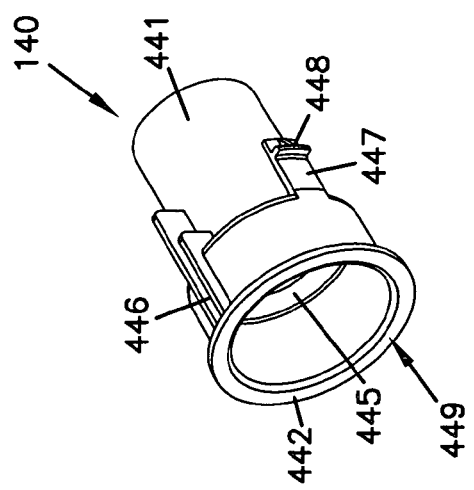
FIG. 14 is a perspective view of a sleeve of the device of FIG. 1.
Figure 18:
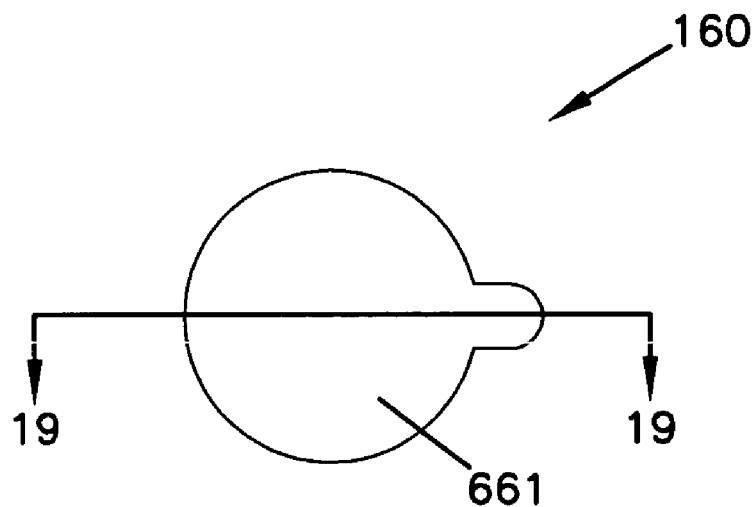
FIG. 18 is a top view of an adhesive portion of the device of FIG. 1.
Figure 19:
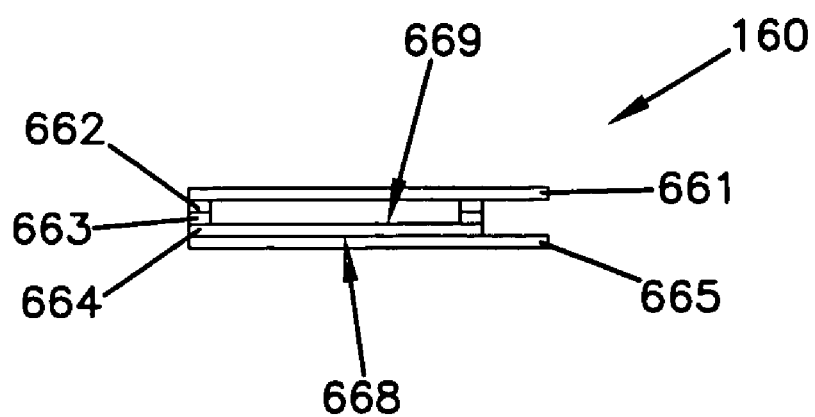
FIG. 19 is a cross-sectional view taken along line 19-19 of the adhesive portion of FIG. 18.
Figure 20:
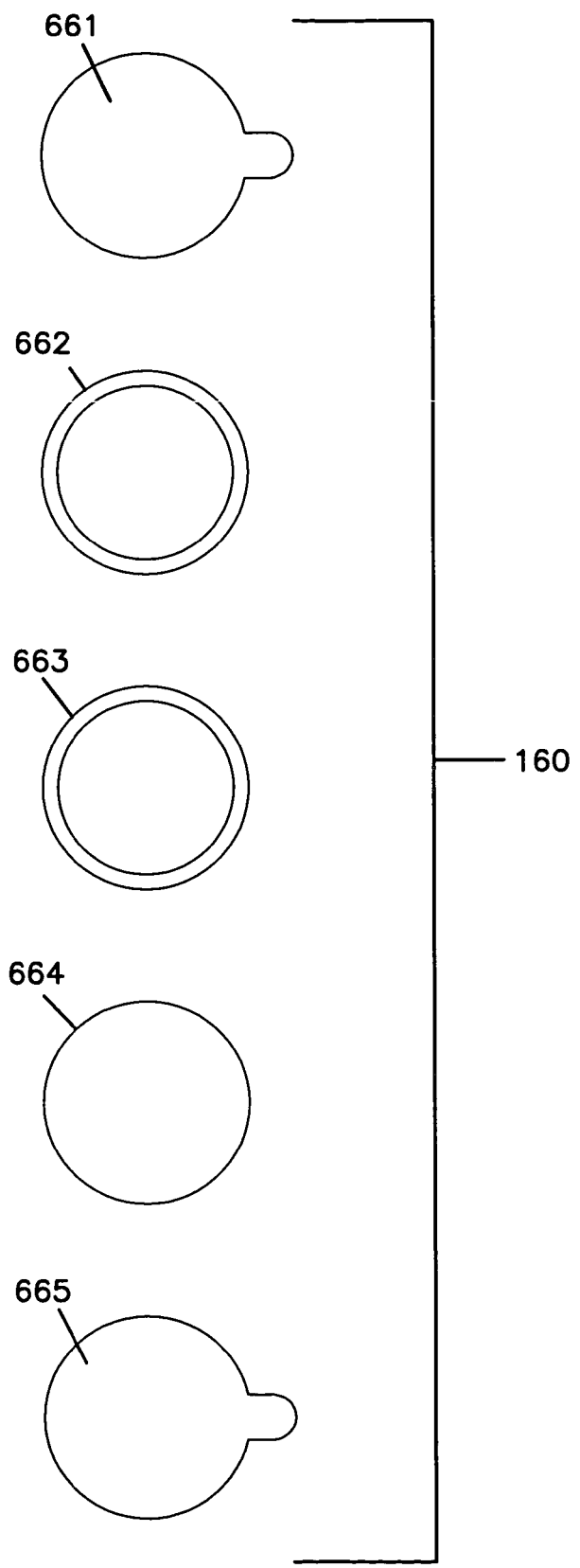
FIG. 20 is an exploded view of the adhesive portion of FIG. 18.

Referring now to FIGS. 18-20, an adhesive portion 160 is positioned on a surface 449 at the second end 442 of the sleeve 140 (see FIGS. 14 and 17). The surface 449 preferably acts as a framework that stabilizes the adhesive portion 160 prior to placement on the patient. In a preferred embodiment shown, the adhesive portion 160 includes layers 662, 663, and 664, as well as liners 661 and 665. Liners 661 and 665 also preferably include tabs that allow for removal of the liners 661 and 665 as described below.

The adhesive portion 160 can be coupled to the surface 449 of sleeve 140 in a variety of manners. In a preferred embodiment, the liner 661 is removed, and layer 662 is coupled to the surface 449 using an adhesive. In addition, as described further below, in a preferred embodiment a top surface 669 of layer 664 and/or a lower end of the infusion device includes an adhesive to couple the infusion device to the adhesive portion 160 as the infusion device is moved into contact with the adhesive portion. See FIGS. 28A, 28B, and 28C.

In addition, the liner 665 is preferably removed, and a lower surface 668 of the layer 664 includes an adhesive to couple the adhesive portion 160 to the skin of the patient.

Preferably, the site is loaded into the device 100 prior to application of the adhesive portion 160 onto the device 100, and preferably both liners 661 and 665 are removed as described above prior to attachment of the adhesive portion to the sleeve 140 and coupling of the cap 170 to the housing 110. In this manner, the patient preferably does not need to remove any liners prior to application of the adhesive portion 160 to the skin and introduction of the site into the skin.

Preferably, the layer 664 does not include any holes, but instead is pierced by the needle 336 as the needle 336 is advanced towards the skin, as described further below. This configuration can enhance the fit between the adhesive portion 160 and the skin of the patient.

In a preferred embodiment, the adhesive portion 160 includes adhesive on one or more of surfaces 668 and 669 to allow the adhesive portion 160 to be coupled to the sleeve 140, site, and/or to the skin of the patient. Typical adhesives that can be used on the adhesive portion 160 include, without limitation, acrylic adhesive, synthetic rubber-based adhesive, acrylate adhesive, and silicone-based adhesive.

In example embodiments, the adhesive portion 160 includes films with adhesives thereon, such as a Tegaderm™ film manufactured by 3M™ or an IV3000™ film manufactured by Smith & Nephew. For example, in the preferred embodiment shown, the tape layer 662 is 3M™ 9731 tape, and layers 663 and 664 are 3M™ Tegader™ p/n 9842.

Figure 22:
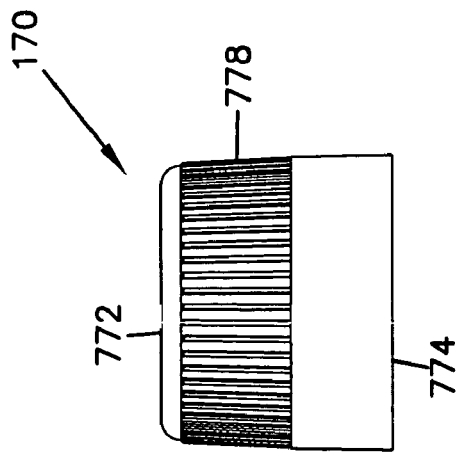
FIG. 22 is a side view of the cap of FIG. 21.
Figure 21:
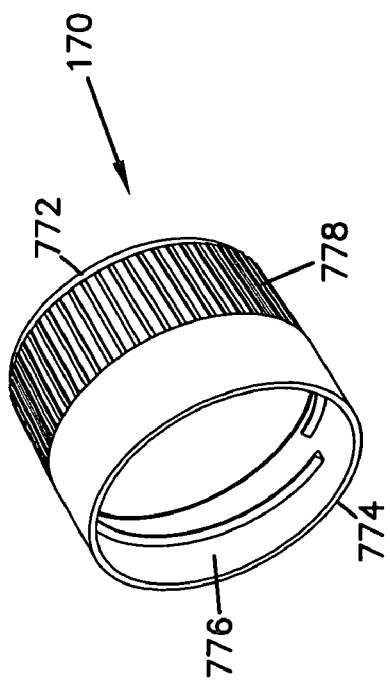
FIG. 21 is a perspective view of a cap of the device of FIG. 1.
Figure 23:
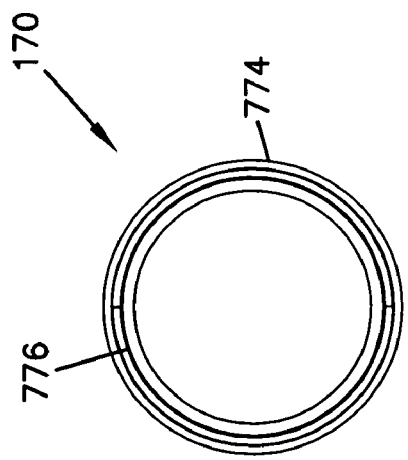
FIG. 23 is an end view of the cap of FIG. 21.

Referring now to FIGS. 21-23, the cap 170 is illustrated. The cap 170 includes a closed first end 772 and an open second end 774. The cap 170 preferably includes an exterior with a knurled surface 778 to enhance the patient's grip on the cap 170. In addition, the interior of the cap 170 includes a threaded portion 776 positioned adjacent the open second end 774 so that the threaded portion 776 can be threaded onto the threaded portion 113 of the housing 110 to seal the device 100. See FIGS. 1, 26A, and 26B.

In a preferred embodiment, a gasket 122 is provided on the threaded portion 113 of the housing 110 to create a seal between the cap 170 and the housing 110 as the cap 170 is threaded onto the housing 110. See FIGS. 26A and 26B. In this manner, the internal components of the device 100 (e.g., needle 336 and site 800) can be maintained in a substantially sterile state prior to removal of the cap 170. Further, the cap 170 can function to maintain the device 100 in a ship state (i.e., the housing 110 can not be moved relative to the sleeve 140) prior to removal of the cap 170 from the housing 110.

In alternative embodiments, the cap 170 and/or housing 110 can be formed to provide a tamper-evident seal so that the patient can determine when the cap 170 has been previously uncoupled from the housing. It can be desirable to provide a tamper-evident seal, for example, so that the patient can assure that the device has not been previously opened and is sterile prior to use.

As previously noted, the device 100 can be used to introduce a cannula of an infusion device into the subcutaneous layer of skin of the patient. In a preferred embodiment, the infusion device includes a site 800, the site 800 including a cannula for delivery of a substance into the subcutaneous layer of skin of the patient. Site 800 is linked by tubing (not shown) with a fluid source, such as an infusion pump (not shown) to deliver fluid to the patient through the cannula. In a preferred embodiment, the site 800 can be made in accordance with that disclosed in U.S. patent application Ser. No. 10/705,736, filed Nov. 10, 2003 and entitled "Subcutaneous Infusion Device and Method," the entirety of which is hereby incorporated by reference. However, sites of other configurations can also be used.

Figure 24:
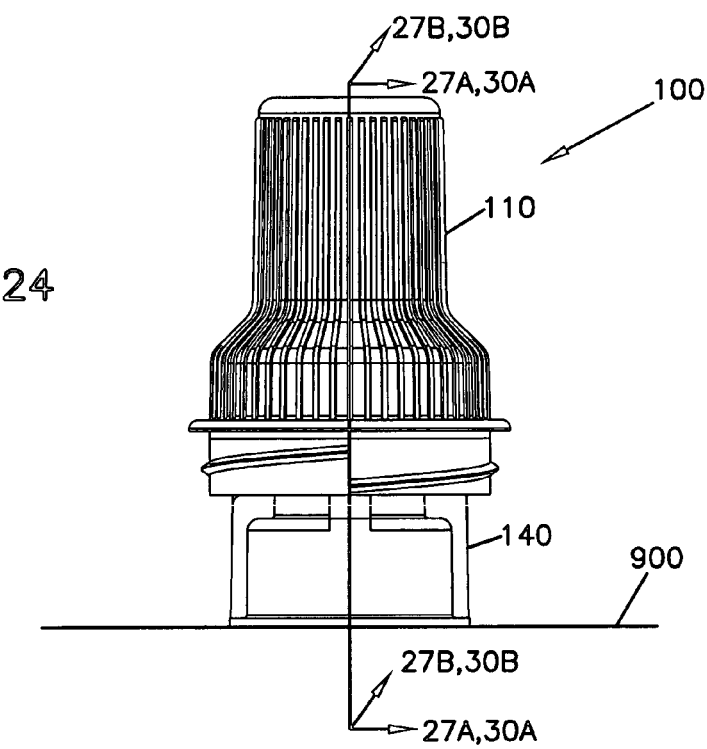
FIG. 24 is a side view of the device of FIG. 1 with the cap removed.
Figure 25:
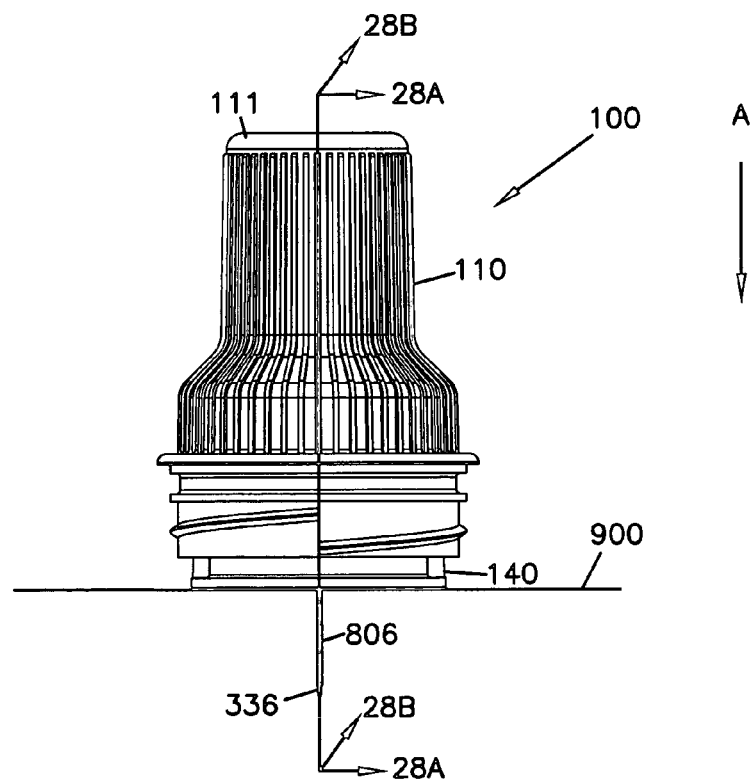
FIG. 25 is a side view of the device of FIG. 24 in a trigger state.

Referring now to FIGS. 1 and 24-30, the device 100 is illustrated in various states of use. As shown in FIGS. 1, 26A, and 26B, the device 100 is in a ship state prior to use. As shown in FIGS. 24, 27A, and 27B, the device 100 is in a delivery state ready to deliver the cannula of an infusion device into the skin of the patient. As shown in FIGS. 25, 28A, 28B, and 28C the device 100 is in a trigger state, or the state at which the needle 336 and the cannula of the site 800 have been fully inserted into the subcutaneous layer of skin of the patient, and the needle hub 130 and associated needle 336 are about to be retracted. As shown in FIGS. 29A and 29B, the device 100 is in a retracted state with the needle hub 130 and associated needle 336 having been retracted into the device 100. As shown in FIGS. 30A and 30B, the device 100 is in a fully retracted state with the housing 110 and sleeve 140 returned to an uncompressed position relative to one another.

Figure 26A:
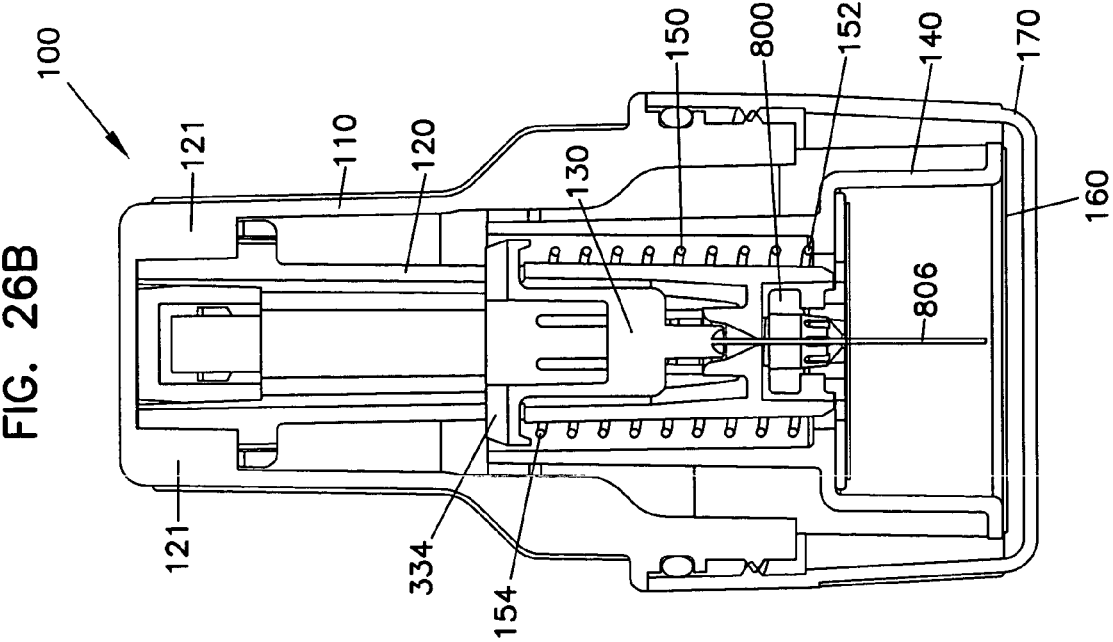
FIG. 26A is a cross-sectional view taken along line 26A-26A of the device of FIG. 1 in a ship state.
Figure 26B:
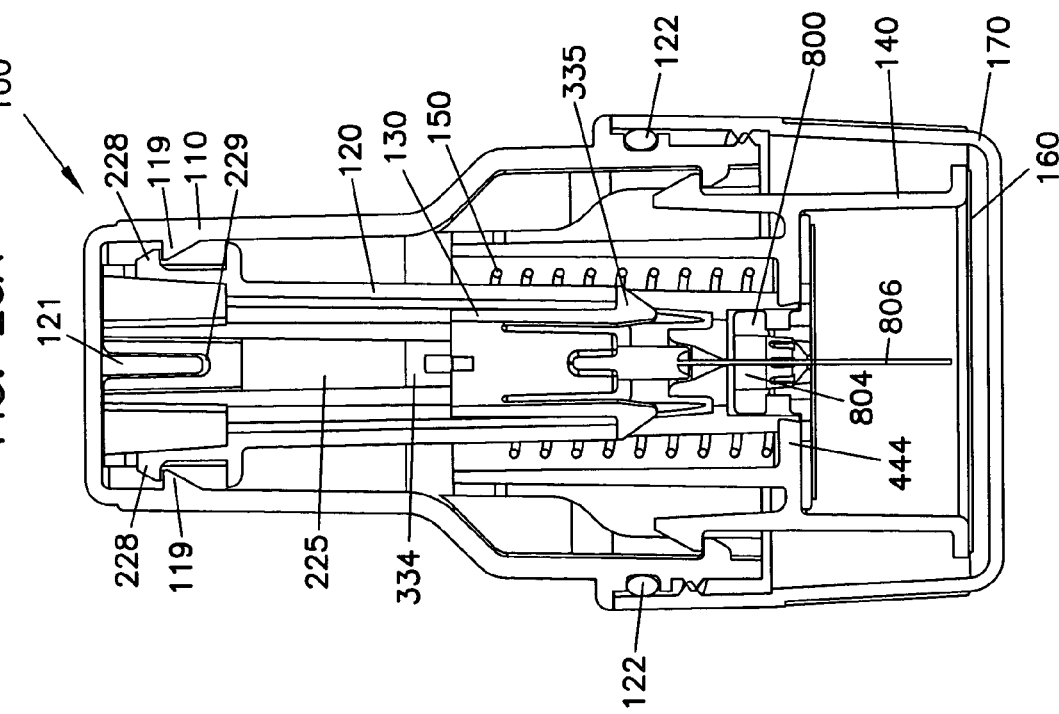
FIG. 26B is a cross-sectional view taken along line 26B-26B of the device of FIG. 1 in the ship state.

An example method of use of the device 100 is as follows. The device 100 is provided to a patient with the cap 170 coupled to the housing 110, as shown in FIGS. 1, 26A, and 26B. Preferably, the site 800 has been previously loaded (i.e., preloaded) into the device 100 during, for example, the manufacturing process for the device 100.

The cap 170 is then unthreaded from the housing 110, and the sleeve 140 of the device 100 is positioned so that the adhesive portion 160 (i.e., surface 668) contacts the skin 900 of the patient. See FIGS. 24, 27A, and 27B.

Next, in the illustrated preferred embodiment, the patient applies pressure to the upper end 111 of the housing 110 to move the housing 110 and associated structures including the cylinder hub 120 and needle hub 130 (including needle 336 and site 800) in a direction A with respect to the sleeve 140 and toward the skin 900 of the patient. As the needle 336 of the needle hub 130 and associated site 800 are moved in the direction A, the needle 336 and the cannula 806 of the site 800 are introduced into the skin 900 of the patient. In addition, as the needle hub 130 is moved toward the sleeve 140, the spring 150 is further compressed.

Once the needle 336 and cannula 806 of the site 800 have been fully inserted into the skin 900, the device 100 is in a trigger state, as illustrated in FIGS. 25, 28A, 28B, and 28C. In this state, the barbs 335 that couple the needle hub 130 to the cylinder hub 120 are biased inwardly through contact with the projections 444 formed by the sleeve 140.

Figure 28C:
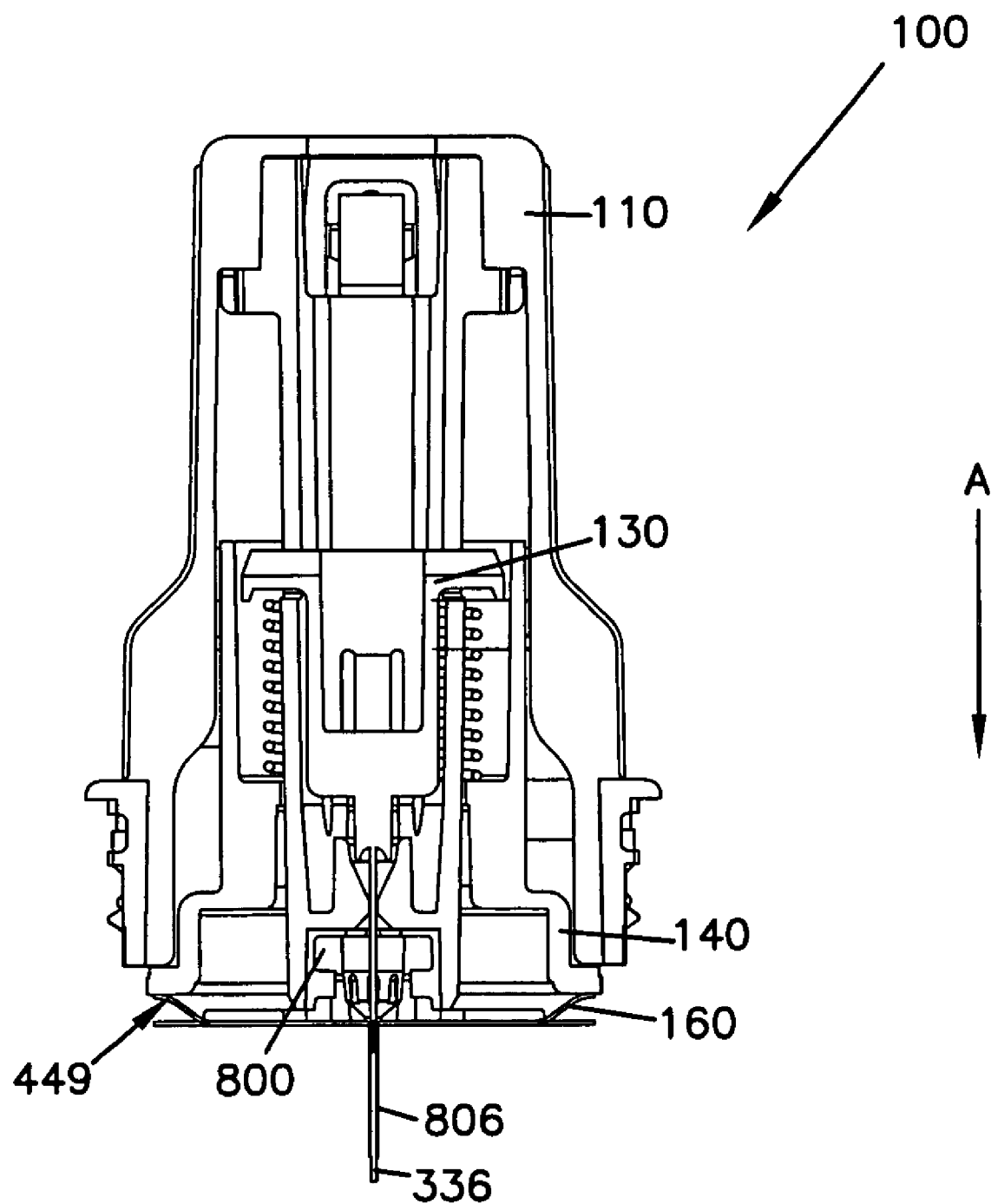
FIG. 28C is a cross-sectional view of the device of FIG. 28B illustrating the adhesive portion being sheared from a surface of the sleeve.

As the housing 110, cylinder hub 120, and needle hub 130 are displaced further in the direction A, it is preferable that the needle hub 130 is positioned so that a lower portion of the site 800 travels slightly beyond the second end 442 of the sleeve 140 as shown in FIG. 28C. This "over-travel" assures that the adhesive portion 160 is properly sheared away from the surface 449 of the sleeve 140 and allows for the coupling of the site 800 to the adhesive portion 160. For example, in preferred embodiments, the lower portion of the site 800 travels beyond the second end 442 of the sleeve 140 by between 50 to 100 thousandths of an inch, more preferably approximately 70 thousandths of an inch.

Figure 29A:
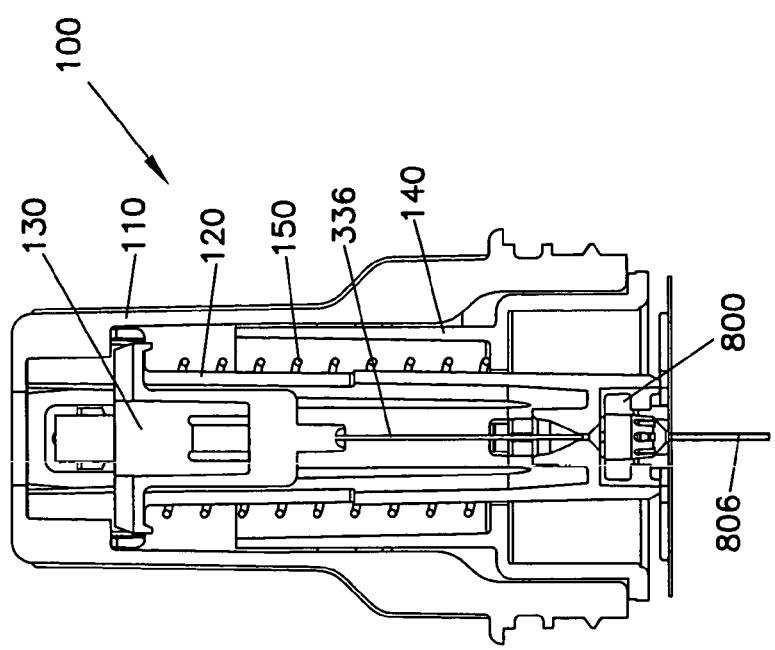
FIG. 29A is a cross-sectional view of the device of FIG. 28A with the needle hub retracted.
Figure 29B:
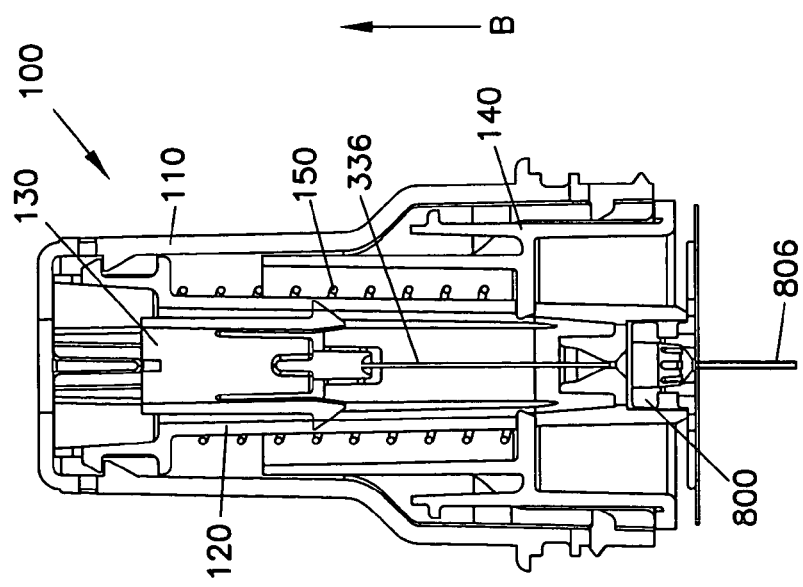
FIG. 29B is a cross-sectional view of the device of FIG. 28B with the needle hub retracted.

In addition, as the housing 110, cylinder hub 120, and needle hub 130 are displaced further in the direction A as described above, barbs 335 of the needle hub 130 are forced inwardly by the projections 444 of the sleeve 140, and the barbs 335 are thereby uncoupled from engagement with the cylinder hub 120. Once the barbs 335 of the needle hub 130 are released from the cylinder hub 120, the needle hub 130 is free to move longitudinally within the passage 223 of the cylinder hub 120 in a direction B opposite to that of the direction A. The spring 150, which has been compressed through the movement of the housing 110 in the direction A, propels the needle hub 130 and associated needle 336 in the direction B up through the cylinder hub 120 into the upper end 111 of the housing 110, while leaving the site 800 and associated cannula 806 positioned in the skin 900 of the patient, as shown in FIGS. 29A and 29B.

Figure 30B:
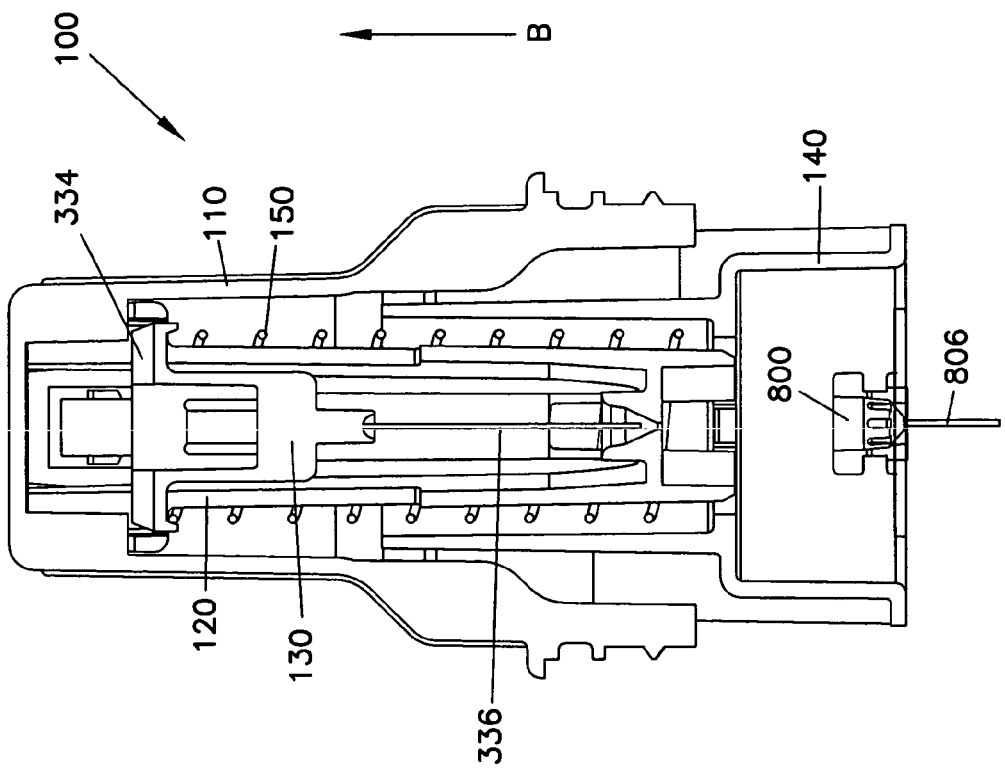
FIG. 30B is a cross-sectional view taken along line 30B-30B of the device of FIG. 24 in the retracted state.
Figure 30A:
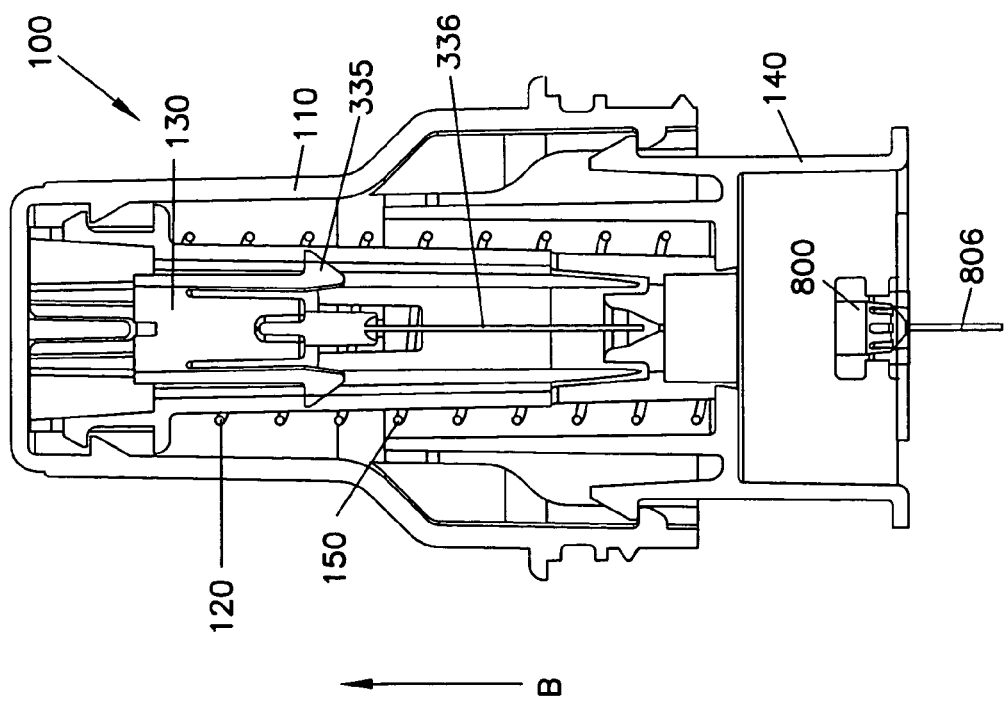
FIG. 30A is a cross-sectional view taken along line 30A-30A of the device of FIG. 24 in a retracted state.

Once the patient removes pressure from the upper end 111 of the housing 110, the spring 150 causes the housing 110 and cylinder hub 120 to move in the direction B as shown in FIGS. 30A and 30B to a fully retracted state.

Finally, the sleeve 140 is removed from contact with the skin 900, and the cap 170 can be replaced onto the threaded portion 113 of the housing 110 of the device 100. Subsequently, the device 100 can be discarded.

Figure 31:
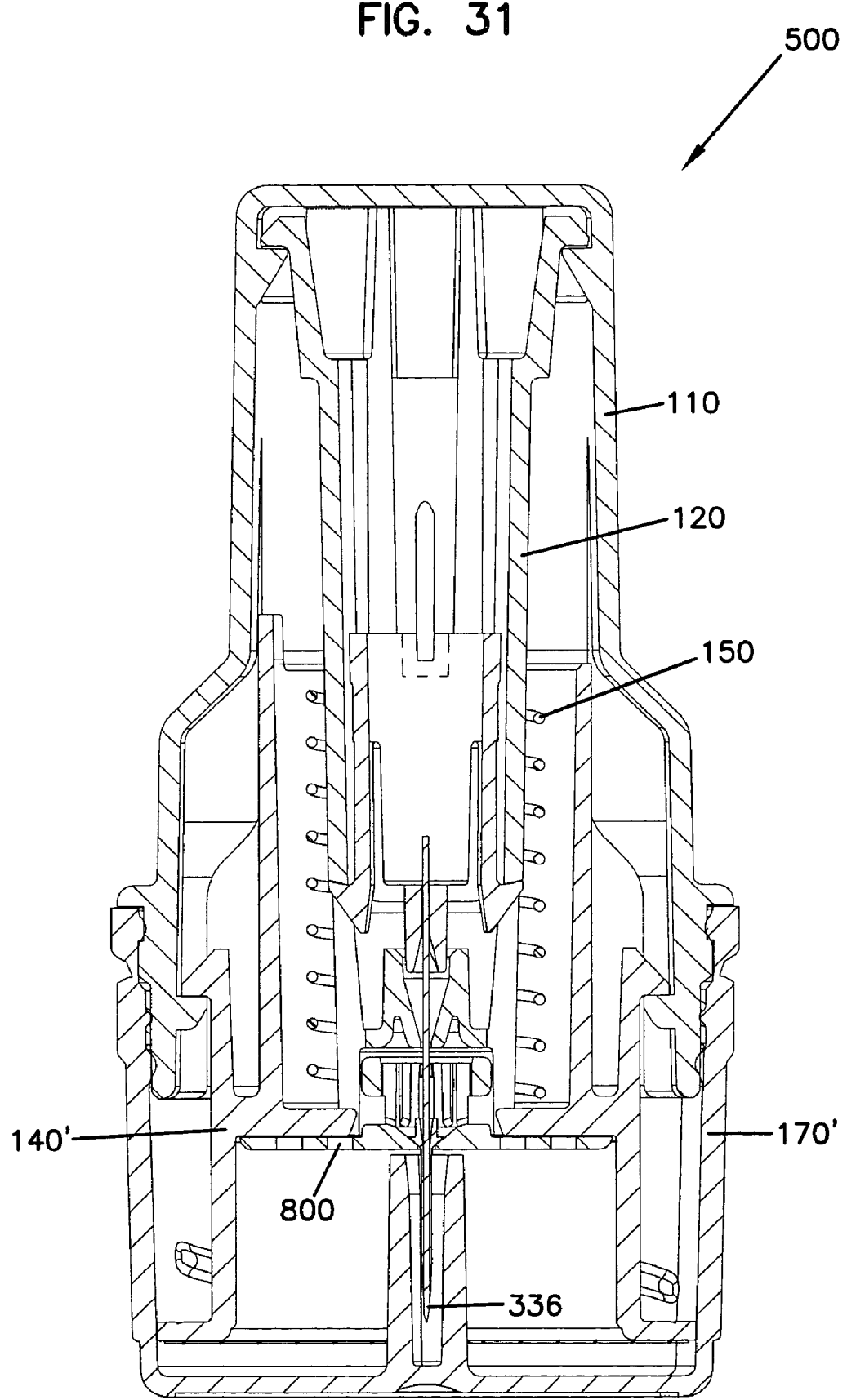
FIG. 31 is a cross-sectional view of another example embodiment of a device used to introduce an infusion device into a patient made in accordance with the present invention.

Many alternative designs for the device can be provided. For example, in FIG. 31 a portion of an alternative device is shown including cylinder hub 120' and needle hub 130'. The cylinder hub 120' and needle hub 130' are similar to cylinder hub 120 and needle hub 130 described above, except that the cylinder hub 120' includes projections 129 formed near the first end 221 of the cylinder hub 120', and the needle hub 130' includes barbs 139 formed on the first end 332. The barbs 139 are configured to ride inside the interior passage 223 of the cylinder hub 120' during retraction of the needle 336 in the direction B until the barbs 139 extend beyond the projections 129 of the cylinder hub 120'. Once this occurs, the barbs 139 expand outward slightly. In this configuration as shown in FIG. 31, the barbs 139 prevent the needle hub 130' and associated needle 336 from being moved back in the direction A. In this manner, the barbs 129 lock the needle hub 130' in the retracted position. This configuration can be beneficial, used separately or in conjunction with the force of the spring 150 forcing the needle hub 130' in the direction B, to further reduce the possibility of inadvertent exposure to the needle 336 after retraction.

Additional details regarding alternative designs for device 100 can be found in U.S. patent application Ser. No. 10/705,725, filed Nov. 10, 2003 and entitled "Device and Method for Insertion of a Cannula of an Infusion Device," the entirety of which is hereby incorporated by reference.

Referring now to FIGS. 31-40, another embodiment of a device 500 is shown. Device 500 is similar to device 100 described above. However, device 500 includes features that retain components of device 500 and/or site 800 contained therein in desired positions while device 500 is in a ship state (i.e., prior to removal of the cap 170' from device 500).

More specifically, in the illustrated embodiment, sleeve 140' and cap 170' of device 500 include features that function to: (i) retain the sleeve 140' in a desired position with respect to the housing 110 while device 500 is in the ship state; and/or (ii) retain the site 800 of an infusion device at a desired position with respect to the needle 336 while the device 500 is in the ship state.

Referring now to FIGS. 32-37, the sleeve 140' is illustrated. Generally, sleeve 140' is similar to sleeve 140 described above, except that sleeve 140' includes tabs 540 spaced about surface 449 at second end 442 of sleeve 140'. In the example shown, four tabs 540 are spaced circumferentially ninety degrees apart about the surface 449. The tabs 540 extend outward radially from the surface 449. More or fewer tabs (e.g., two tabs or one tab) can also be used.

Referring now to FIGS. 32, 33, and 38-40, tabs 540 on sleeve 140' are configured to engage beads 510 formed adjacent closed first end 772 of cap 170' when the device 500 is in the ship state (i.e., with cap 170' threaded onto device 500). In the illustrated embodiment, cap 170' includes four beads 510 formed on an internal surface of the cap 170'. The beads 510 are pitched at an angle and spaced circumferentially ninety degrees apart about the cap 170'. In alternative designs, more or fewer beads (e.g., two beads or one bead) can also be used.

In the illustrated embodiment, beads 510 are formed to correspond to tabs 540 on the sleeve 140'. Spaces 512 (see FIG. 40) are formed between adjacent beads 510. Spaces 512 allow the tabs 540 to pass between and clear the beads 510 when the cap 170' is placed onto the device 500 and threaded onto the housing 110 during manufacture.

Figure 32:
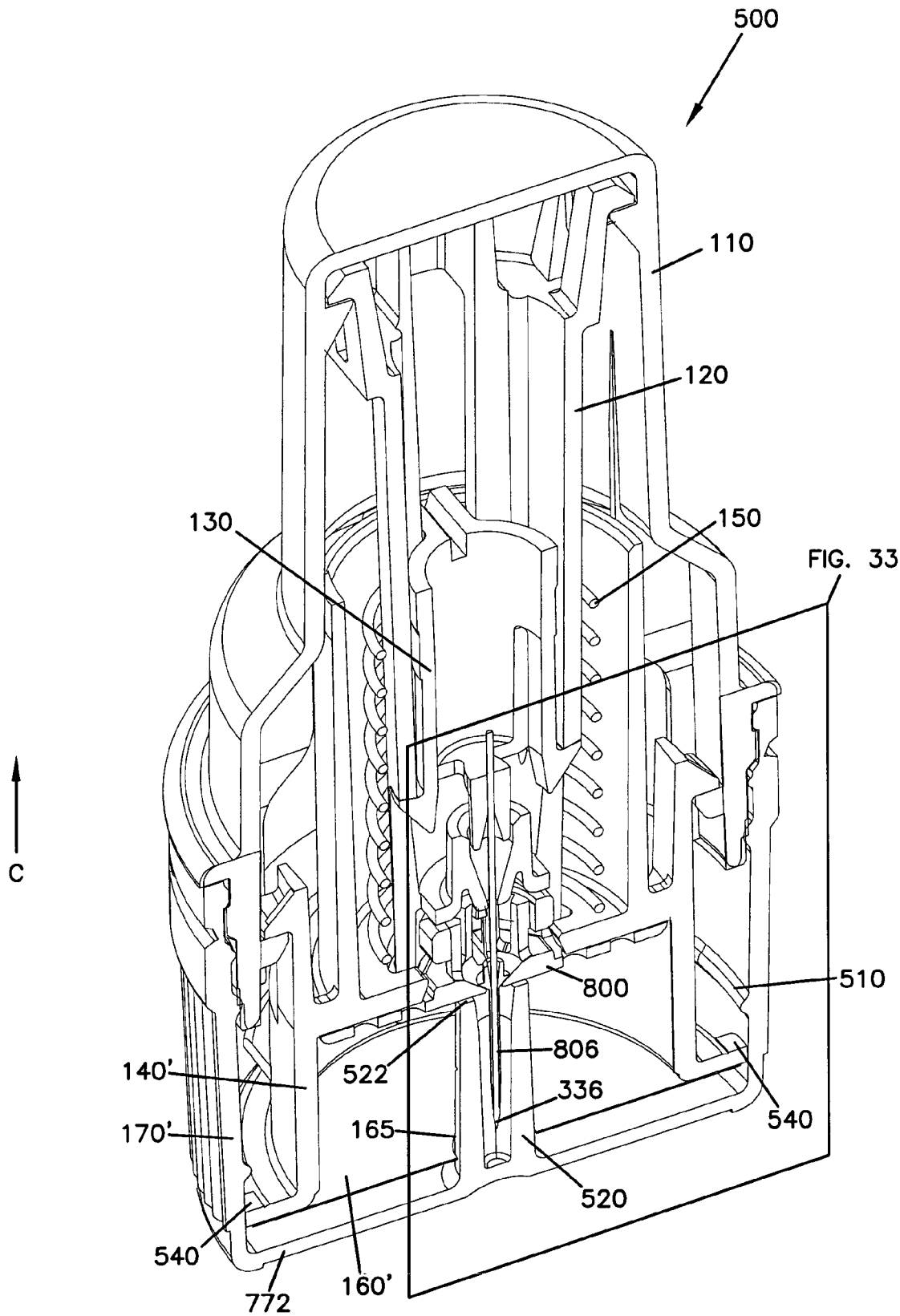
FIG. 32 is a perspective cross-sectional view of the device of FIG. 31.
Figure 33:
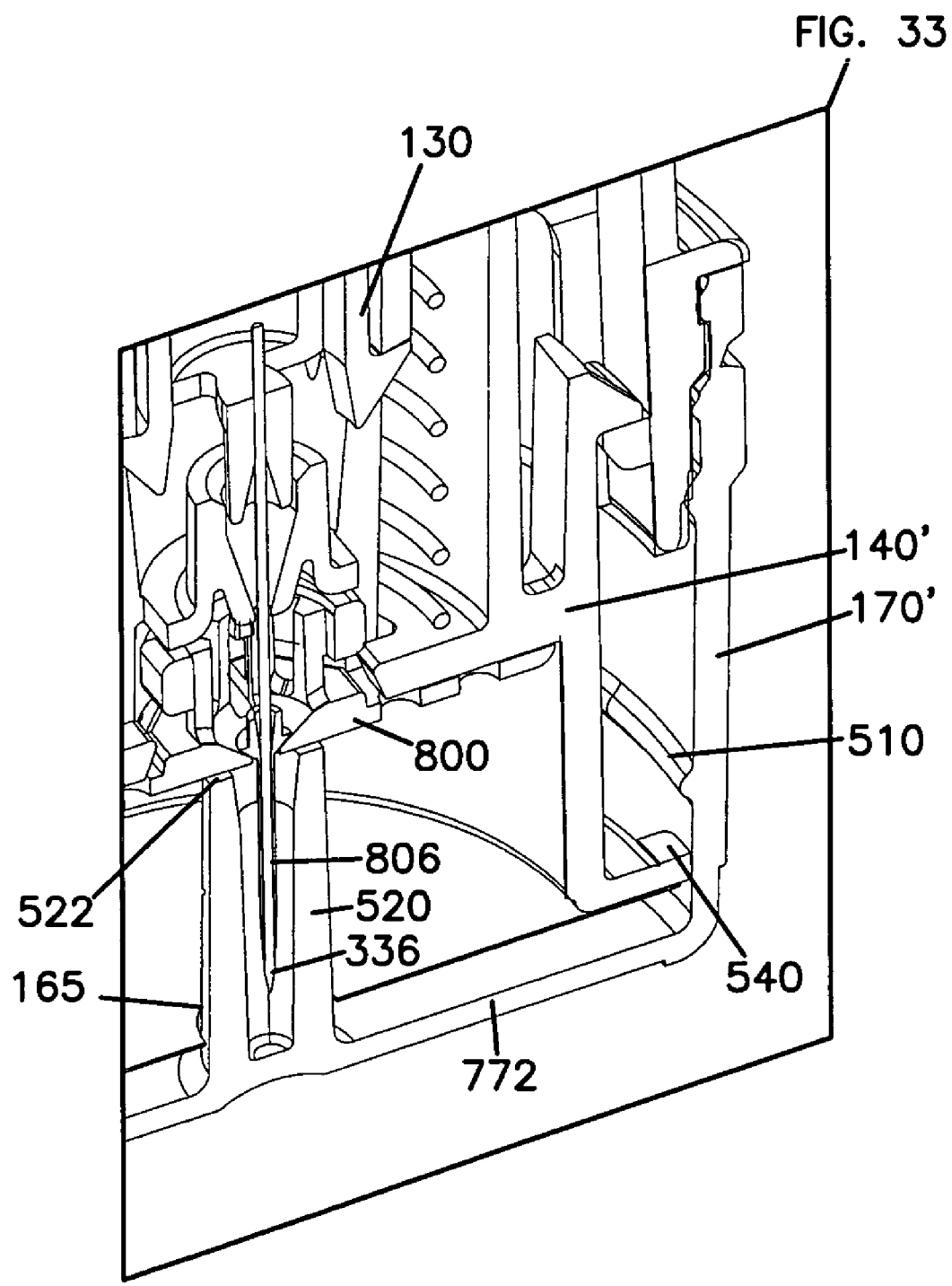
FIG. 33 is a perspective cross-sectional view of a portion of the device of FIG. 32 in enlarged form.
Figure 34:
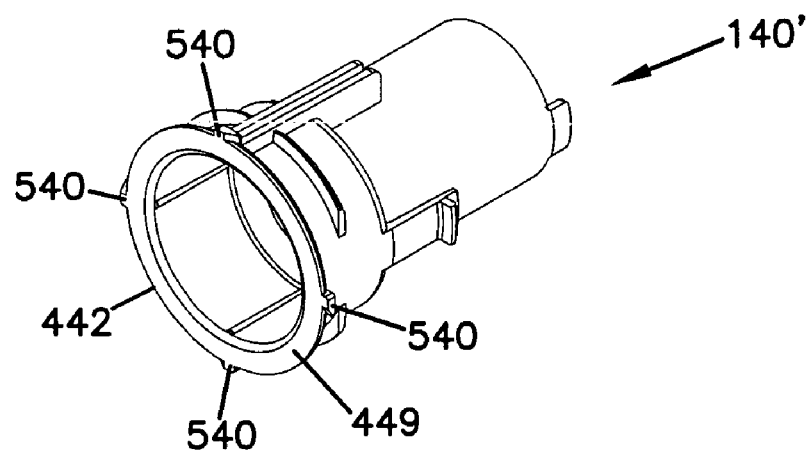
FIG. 34 is a perspective view of a sleeve of the device of FIG. 31.
Figure 35:
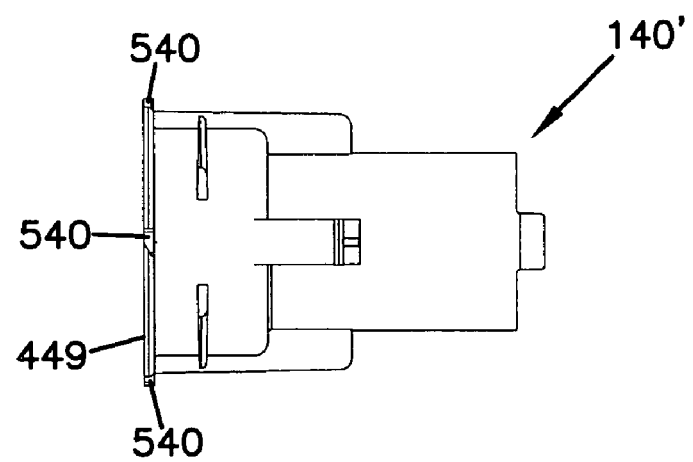
FIG. 35 is a side view of the sleeve of FIG. 34.
Figure 39:
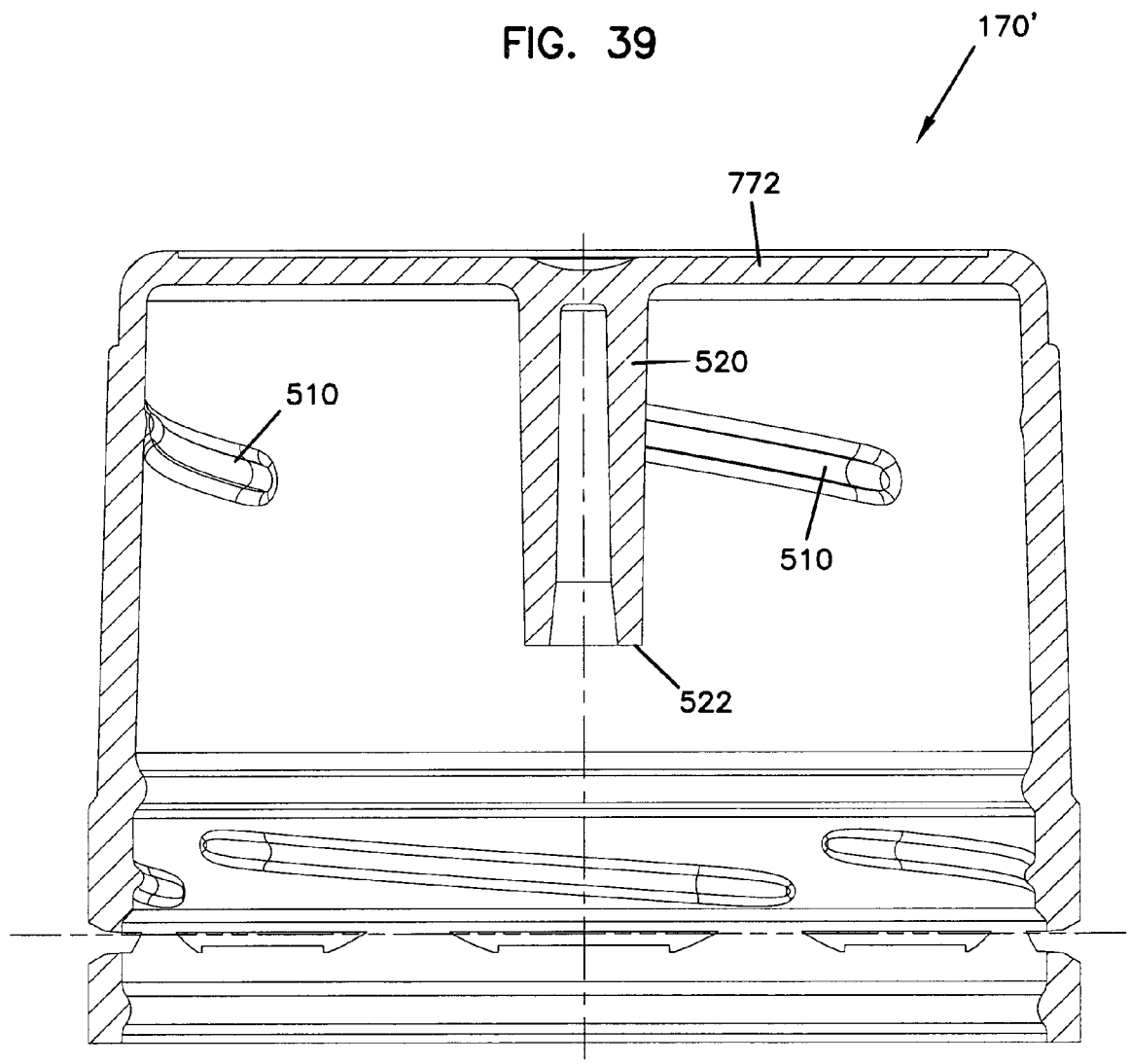
FIG. 39 is a cross-sectional view taken along line 39-39 of the cap of FIG. 38.
Figure 40:
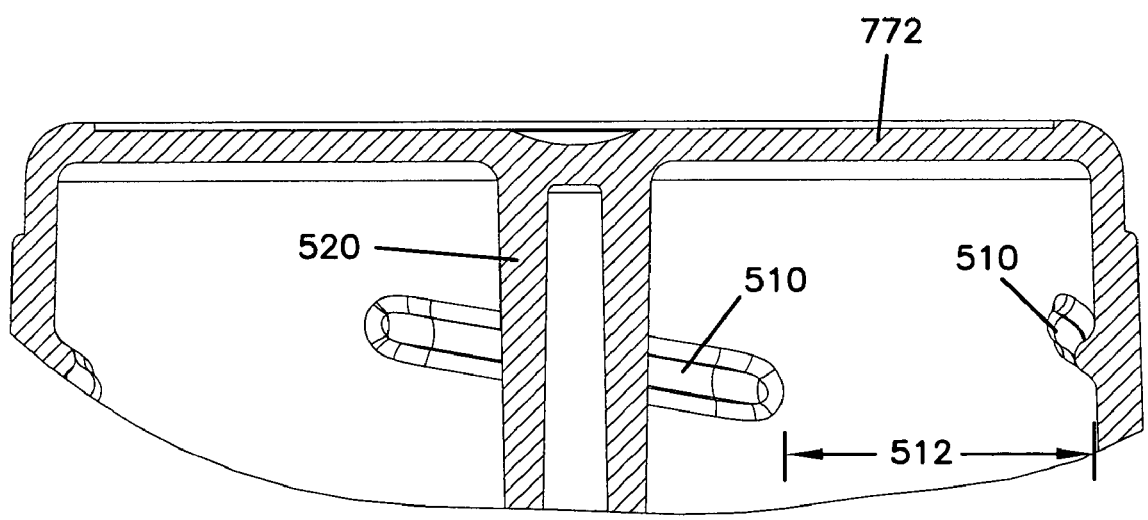
FIG. 40 is a cross-sectional view taken along line 40-40 of a portion of the cap of FIG. 38 in enlarged form.

Once the device 500 is in the ship state shown in FIGS. 31-33, the tabs 540 and beads 510 function to maintain the device 500 in the ship state. If the sleeve 140' moves in a direction C while the device 500 is in the ship state (due to, for example, a sudden shock caused by dropping or otherwise jarring the device 500), tabs 540 of the sleeve 140' contact beads 510 of the cap 170', thereby limiting further movement of the sleeve 140' in direction C. In this manner, device 500 is maintained in the ship state, and inadvertent movement of the sleeve 140' to the trigger state and resulting retraction of the needle hub 130 can be avoided.

When device 500 is ready for use and cap 170' is unthreaded from the housing 110, tabs 540 ride along the pitch of beads 510 until tabs 540 reach spaces 512 between adjacent beads 510, which allow tabs 540 to clear beads 510 and cap 170' to be removed from housing 110.

Referring back to FIGS. 32, 33, and 38-40, cap 170' also includes a boss 520 extending from closed first end 772 of cap 170'. In the illustrated embodiment, boss 520 is cylindrical and forms a central cavity sized to receive needle 336 and cannula 806 of the site 800. A free end 522 of the boss 520 extends to a point adjacent to a bottom surface of the site 800 when the site 800 is in the preloaded position (i.e., the site 800 having been loaded into the device 500 during, for example, the manufacturing process). If the site 800 travels slightly downward on the needle 336, the bottom surface of the site 800 contacts the free end 522 of the boss 520, thereby limiting further travel of the site 800. Therefore, if the device 500 receives a shock while in the ship state, which can potentially cause the site 800 to slide downward relative to the needle 336, the boss 520 contacts and maintains the site 800 at a desired position with respect to the needle 336.

In the illustrated embodiment shown in FIGS. 32 and 33, adhesive portion 160' forms an aperture 165 sized to allow the boss 520 to extend therethrough.

Referring now to FIGS. 41-45, an alternative embodiment of a device 600 is shown. Device 600 is similar to device 500 described above, except that device 600 includes a clip 650. Clip 650 includes a main body 625 and projections 610 that extend through apertures 620 formed in sleeve 640.

Figure 41:
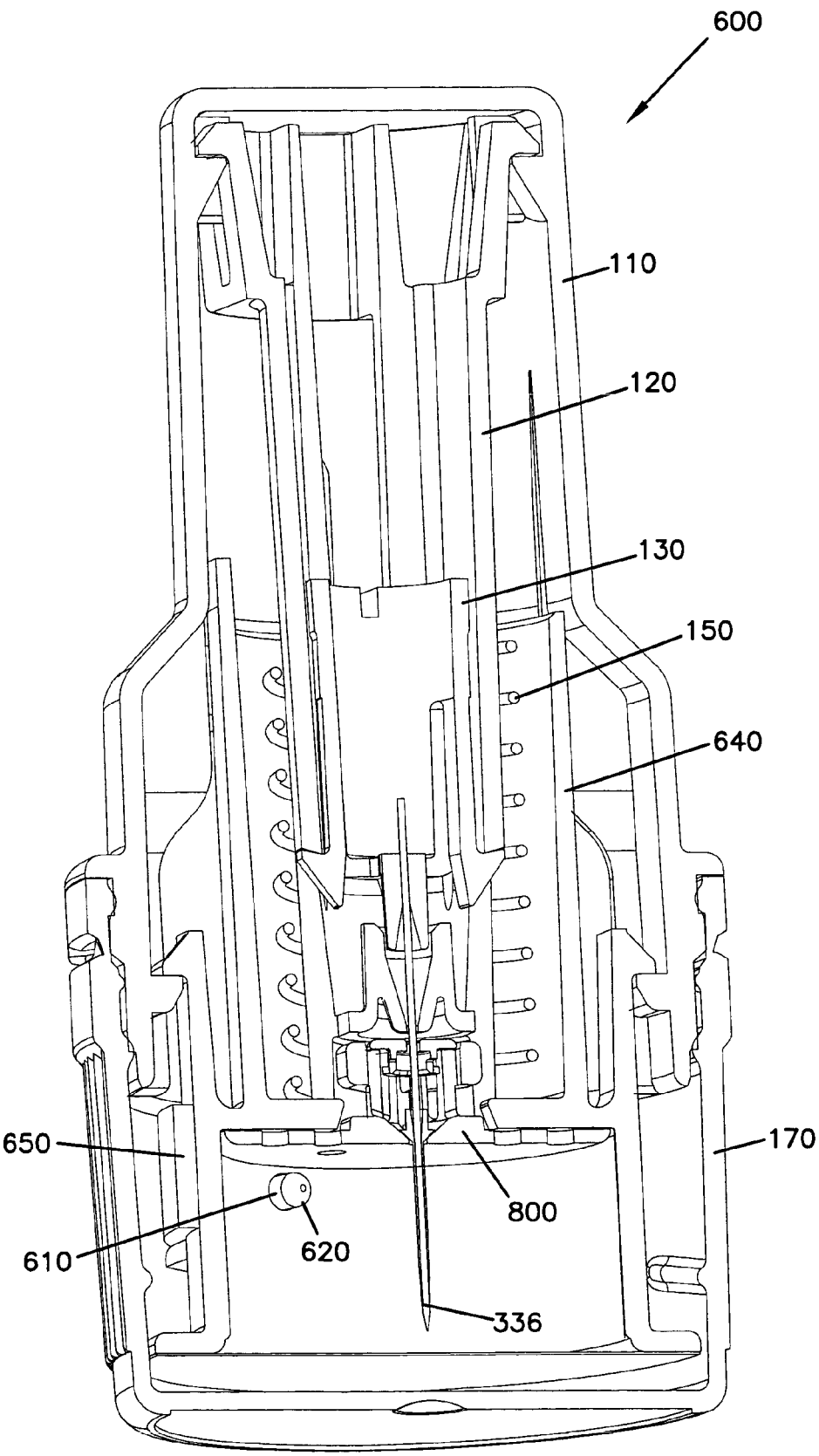
FIG. 41 is a cross-sectional view of another example embodiment of a device used to introduce an infusion device into a patient made in accordance with the present invention.
Figure 42:
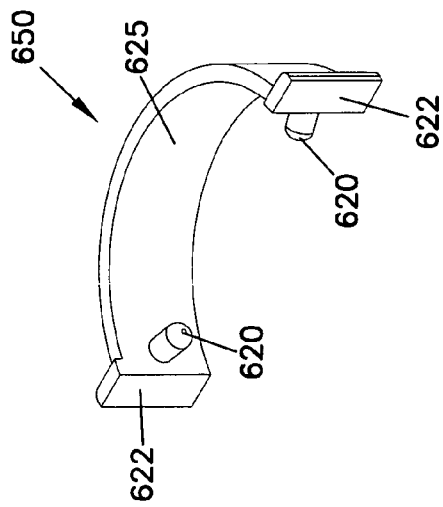
FIG. 42 is a perspective view of a clip of the device of FIG. 41.
Figure 43:
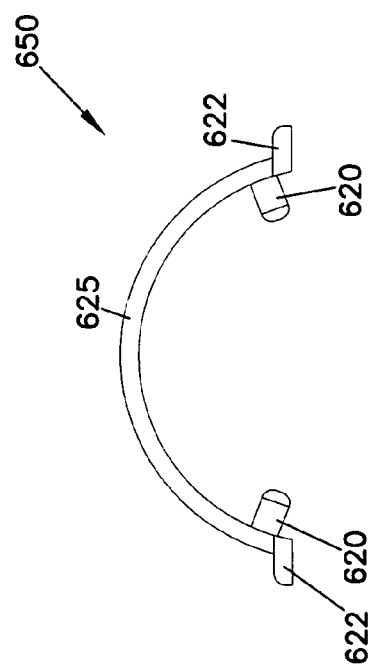
FIG. 43 is a top view of the clip of FIG. 42.
Figure 44:
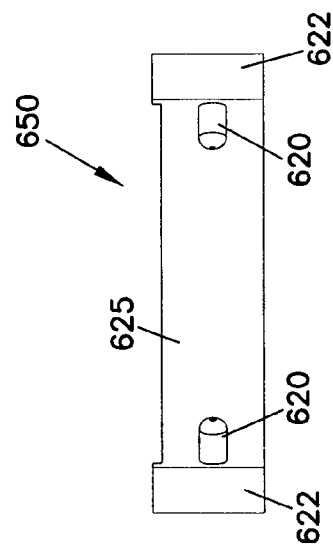
FIG. 44 is a side view of the clip of FIG. 42.
Figure 45:
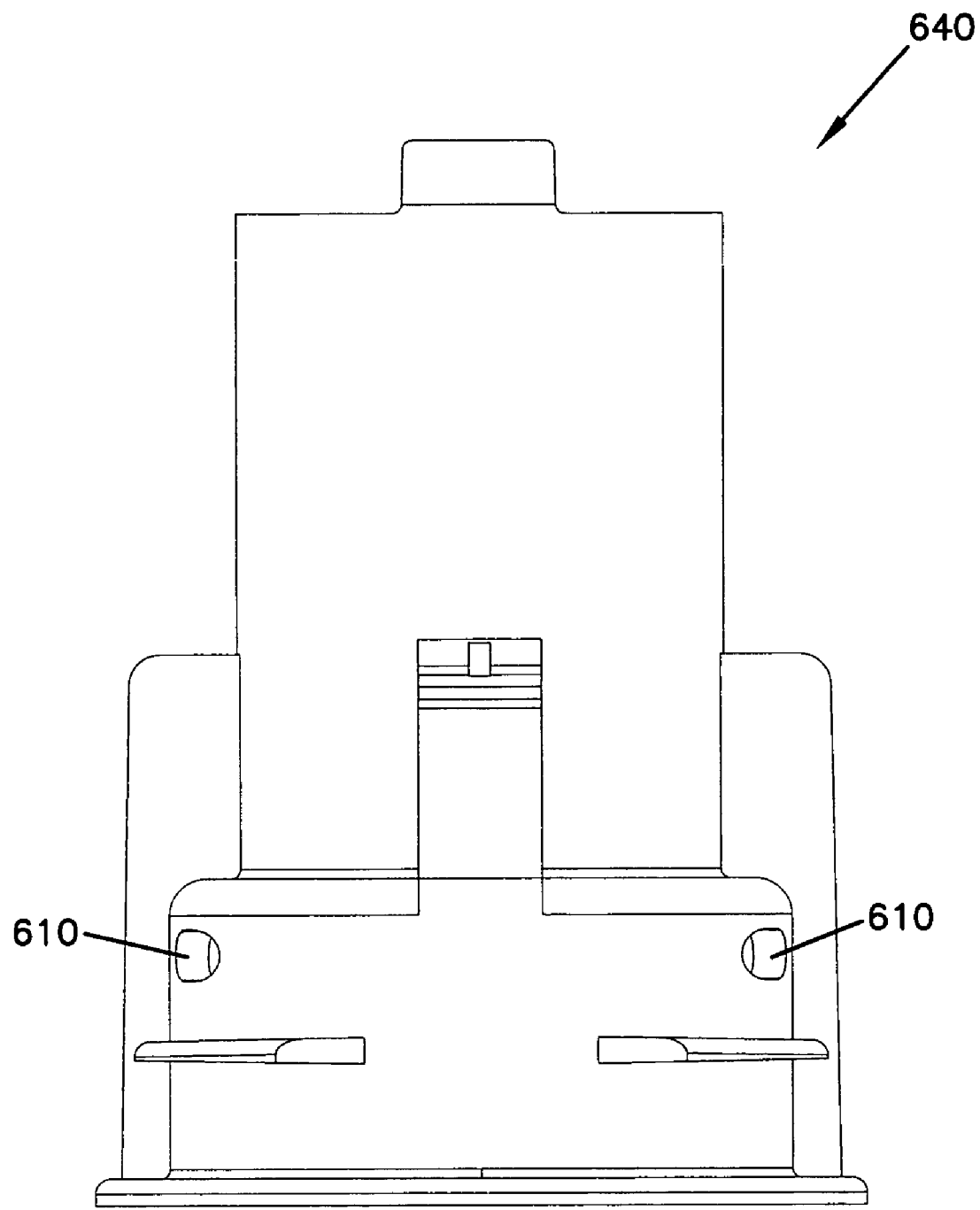
FIG. 45 is a side view of a sleeve of the device of FIG. 41.

With the clip 650 positioned on the sleeve 640 as shown in FIG. 41, the projections 610 extend partially below a bottom surface of the site 800 and thereby function to engage the bottom surface of the site 800 if the site 800 travels downward on needle 336. In addition, if the sleeve 640 is moved relative to the housing 110 while the clip 650 is in place on the device 600, the projections 610 contact the site 800 to thereby limit further movement of sleeve 640 relative to the housing 110.

When the device 600 is ready for use, the cap 170 is removed. The user can then remove the clip 650 from the device 600 by grasping tabs 622 (see FIG. 42-44) and pulling the projections 610 out of apertures 620. Once the clip 650 is removed from device 600, the sleeve 640 can be moved relative to the housing 110 to introduce the cannula of the site 800 into the skin.

In alternative embodiments, the clip 650 can be replaced by a pin that is extended through apertures in the sleeve and/or housing to retain the sleeve and/or site in place prior to removal of the pin. In other embodiments, tape can be used instead of the clip. For example, tape can be positioned to extend across channels 446 formed in the sleeve 140. See FIGS. 14-17. In this configuration, the tape can limit travel of the railways 114 of the housing in the channels 446 of the sleeve 140, thereby fixing the sleeve relative to the housing.

Further, in the illustrated embodiments, the boss is formed as an integral part of the cap. However, in other embodiments, the boss can be formed separate from the cap. For example, the boss can be formed as a cylindrical piece that is positioned between the site and the cap. In other embodiments, the boss can replace by one or more projections or pillars that extend from the base of the cap up to a point adjacent to the bottom side of the site.

Devices made in accordance with the principles described herein can be advantageous for various reasons. For example, each device can provide ease in placement of the site on the skin, preferably allowing the user to place the site with the device where desired on the body using a single hand to operate the device.

Further, several embodiments disclosed herein include structures that cover or hide the needle prior to insertion of the site, and also cause the needle to be retracted into the device after insertion to protect against inadvertent contact with the needle.

In addition, several embodiments of the devices disclosed herein can automatically retract the needle while leaving the site placed on the skin, thereby reducing the patient's contact with the exposed needle. Preferably, this retraction is automatic in that once the device reaches the trigger state there is no further action required by the patient to cause the needle to be retracted. The automatic retraction of the needle also limits the dwell time of the needle in the patient, increasing comfort for the patient.

In addition, the action of inserting the needle into position on the skin using the devices disclosed herein can function to hold the site on the surface of the skin during needle retraction. This can assist in adherence of the adhesive portion to the skin and reduce the chances of separation between the adhesive portion and site and the skin during needle retraction.

In addition, the housing and cap of several of embodiments of the devices disclosed herein allow the various components of the devices including the needle and infusion device to be delivered to the patient in a self-contained, sterile environment prior to use. The configuration further minimizes the need for packaging surrounding the devices, reducing manufacturing cost and increasing ease in use of the devices. The configuration also allows the housing and cap to protect and maintain the infusion device on the needle of the device. The configuration and disposable nature of the devices further allow ease in discarding of the devices after use.

Also, the configuration of several embodiments of the devices disclosed herein can allow the site to be preloaded into the device, thereby providing ease of use for the patient and reducing the patient's exposure to the needle. For example, single-use embodiments disclosed herein preferably do not require that the patient load the site into the device prior to insertion, but instead provide the device with the site preloaded.

Some embodiments of the devices allow for both automatic delivery of the site and withdrawal of the needle, thereby automating the entire introduction process for the patient.

While single use devices are preferred, reusable devices wherein the needle retracts but can be reloaded are also anticipated.

The above specification, examples and data provide a complete description of the manufacture and of the invention. Since many embodiments of the invention can be made without departing from the spirit and scope of the invention, the invention resides in the claims hereinafter appended.

What is claimed is:

1. A device for inserting a subcutaneous infusion device into skin of a patient, comprising:
    a housing;
    a needle hub including a needle;
    a sleeve;
    a cap coupled to the housing, the cap defining a bead, and the cap defining a boss extending from a closed end of the cap, the boss defining a central cavity sized to receive the needle and associated cannula of the infusion device; and
    a retention member including a tab extending outward radially from the sleeve and configured to engage the bead defined by the cap to limit movement of the sleeve relative to the housing while the cap is coupled to the housing so that the sleeve is prevented from moving to a trigger state;
    wherein a free end of the boss of the cap engages a bottom surface of the infusion device to limit movement of the infusion device relative to the needle while the cap is coupled to the housing; and
    wherein, upon removal of the cap, the needle hub is movable relative to the sleeve to introduce the needle of the needle hub and associated cannula of an infusion device into a subcutaneous layer of skin.

2. The device of claim 1, wherein the retention member comprises four tabs and the cap defines four corresponding beads.

3. The device of claim 1, wherein the bead is defined on an internal circumference of the cap.

4. The device of claim 3, wherein the bead is pitched.

5. The device of claim 1, further comprising a spring engaging the needle hub, wherein, upon the needle and associated cannula of the infusion device being fully inserted into the subcutaneous layer of skin, the needle hub is slideable relative to the sleeve, and the needle hub including the needle are moveable by the spring to a retracted state, leaving the cannula of the infusion device positioned on the skin of the patient.

6. A device for inserting a subcutaneous infusion device into skin of a patient, comprising:
    a housing;
    a needle hub including a needle with a cannula of an infusion device coupled thereto;
    a sleeve defining a tab extending outward radially therefrom; and
    a cap coupled to the housing, the cap defining a boss extending from a closed end of the cap, the boss defining a central cavity sized to receive the needle and associated cannula of the infusion device, and the cap defining a bead on an internal surface of the cap;

wherein a free end of the boss engages a bottom surface of the infusion device to limit movement of the infusion device relative to the needle;

wherein the tab engages the bead defined by the cap to limit movement of the sleeve relative to the housing so that the sleeve is prevented from moving to a trigger state; and wherein, upon removal of the cap, the needle hub is movable relative to the sleeve to introduce the needle of the needle hub and associated cannula of an infusion device into a subcutaneous layer of skin.

7. The device of claim 6, wherein the bead is pitched.

8. The device of claim 6, wherein the sleeve includes four tabs and the cap defines four corresponding beads.

9. A device for inserting a subcutaneous infusion device into skin of a patient, comprising:
 a housing;
 a needle hub including a needle, the needle having a cannula of an infusion device coupled thereto;
 a sleeve;
 a spring engaging the needle hub;
 a cap coupled to the housing;
 a boss coupled to the cap and configured to engage a bottom surface the infusion device to fix the infusion device relative to the needle prior to decoupling of the cap from the housing, wherein the boss is cylindrical and centrally located with respect to a closed end of the cap, and wherein the boss defines a central cavity sized to receive the needle and associated cannula of the infusion device; and
 a tab extending outward radially from the sleeve, wherein the tab engages a bead defined by the cap to limit movement of the sleeve relative to the housing while the cap is coupled to the housing so that the sleeve is prevented from moving to a trigger state, wherein the bead is defined on an internal circumference of the cap;

wherein, upon removal of the cap, the needle hub is movable relative to the sleeve to introduce the needle of the needle hub and associated cannula of the infusion device into a subcutaneous layer of skin, and wherein, upon the needle and associated cannula of the infusion device being fully inserted into the subcutaneous layer of skin, the needle hub is slideable relative to the sleeve, and the needle hub including the needle are moveable by the spring to a retracted state, leaving the cannula of the infusion device positioned on the skin of the patient.

10. The device of claim 9, wherein the bead is pitched.

11. An apparatus, comprising:
 an infusion device including a cannula; and
 a device for inserting the infusion device into skin of a patient, including:
  a housing;
  a needle hub including a needle with the cannula of the infusion device coupled thereto;
  a sleeve defining a tab extending outward radially therefrom; and
  a cap coupled to the housing, the cap defining a boss extending from a closed end of the cap, the boss defining a central cavity sized to receive the needle and associated cannula of the infusion device, and the cap defining a bead on an internal surface of the cap;
 wherein a free end of the boss engages a bottom surface of the infusion device to limit movement of the infusion device relative to the needle while the cap is coupled to the housing; and
 wherein the tab engages the bead defined by the cap to limit movement of the sleeve relative to the housing while the cap is coupled to the housing so that the sleeve is prevented from moving to a trigger state.

12. The apparatus of claim 11, wherein the sleeve includes four tabs and the cap defines four corresponding beads.

* * * * *